United States Patent [19]

Battaglia et al.

[11] 4,214,968

[45] Jul. 29, 1980

[54] ION-SELECTIVE ELECTRODE

[75] Inventors: Charles J. Battaglia; Jack C. Chang; Daniel S. Daniel, all of Rochester, N.Y.

[73] Assignee: Eastman Kodak Company, Rochester, N.Y.

[21] Appl. No.: 893,656

[22] Filed: Apr. 5, 1978

Related U.S. Application Data

[63] Continuation-in-part of Ser. No. 687,966, May 19, 1976, abandoned.

[51] Int. Cl.² .................... G01N 27/30; G01N 27/46
[52] U.S. Cl. .............................................. 204/195 M
[58] Field of Search ............ 204/195 M, 195 F, 195 L, 204/195 G

[56] References Cited

U.S. PATENT DOCUMENTS

| | | | |
|---|---|---|---|
| 3,649,506 | 3/1972 | Petersen et al. | 204/195 G |
| 3,753,887 | 8/1973 | Kadem et al. | 204/195 M |
| 3,856,649 | 12/1974 | Genshaw et al. | 204/195 M |
| 3,926,764 | 12/1975 | Ruzicka et al. | 204/195 F |

*Primary Examiner*—G. L. Kaplan
*Attorney, Agent, or Firm*—Arthur H. Rosenstein

[57] ABSTRACT

A dry-operative ion-selective electrode comprising:
(a) a dried, internal reference electrode, and
(b) in contact with the reference electrode, a hydrophobic ion-selective membrane.

The ion-selective electrode described herein requires no preconditioning prior to use in an ion-sensing operation.

The reference electrode may comprise either a metal/metal salt reference half-cell or multiple-layer redox couple reference electrode. The hydrophobic membrane includes a binder having dispersed therein a solution of an ion carrier dissolved in a suitable carrier solvent.

A preferred embodiment provides for electrodes of the type described wherein the hydrophobic membrane layer is of a predetermined, uniform thickness in regions thereof intended for contact with a sample for analysis. When necessary or desirable, the electrode includes a support. A novel technique for making measurements of ion concentration by reading electrode potential prior to equilibration of the electrode is also described.

30 Claims, 3 Drawing Figures

ION-SELECTIVE ELECTRODE

This is a continuation-in-part of our co-pending application Ser. No. 687,966, filed May 19, 1976, and now abandoned.

BACKGROUND OF THE INVENTION

1. Field of the Invention

This invention relates to analytical measurement and in particular to electrodes for determining specific ion concentrations in solution. More specifically, this invention relates to multilayer elements for use in the potentiometric determination of ion concentrations in aqueous liquids, particularly body fluids such as blood sera.

2. Description of Related Art

The related art is replete with a great variety of electrode types and structures for the measurement of various ions in solution. Typically, devices for obtaining such measurements include a reference electrode and a separate ion-selective electrode. When simultaneously immersed into the same body of solution to be analyzed, the reference and ion-selective electrodes constitute an electrochemical cell, across which a potential develops. This potential is proportional to the logarithm of the activity of the ion of choice which is related to concentration in the solution of the ion of choice to which the ion-selective electrode is sensitive. The foregoing relationship between the potential and ionic activity in solution is described by the well-known Nernst equation. An electrometric device, usually either a direct reading circuit or a null-balance potentiometric circuit, is employed for measuring the potential between the electrodes.

In the past, the ion-sensitive electrode generally comprised an electrode body (usually same type of glass container) containing a known reference solution in contact with a half-cell of known potential, generally Ag/AgCl/"XMCl" and an ion-selective glass membrane mounted in an aperture in the electrode body in such a fashion that, when the electrode was immersed in the unknown solution, the glass membrane contacted both the reference solution within the electrode body and the unknown solution. An appropriate metal probe coated with a layer of an insoluble salt of the metal immersed in the contained reference solution served as the contact while providing a reference potential for the electrode. The selectivity of the electrode was determined by the composition or components of the glass membrane. Such electrodes are referred to herein as "barrel" electrodes. U.S. Pat. Nos. 3,598,713 and 3,502,560 provide detailed descriptions of electrodes of this type.

More recently, the development of synthetic, polymeric ion-selective membranes as substitutes for the ion-selective glass membrane has broadened the list of ions which can be determined potentiometrically using "barrel" electrodes. Such membranes generally comprise a polymeric binder or support impregnated with a solution of an ion-selective carrier or ionophore in a solvent for the ionophore. Membranes of this type can be custom-designed to sense selectively a particular ion by careful selection of the ionophore, solvent, etc. Membranes of this type and "barrel" electrodes containing such membranes as substitutes for the glass membranes are described in detail in the following U.S. Pat. Nos.:

3,562,129 to Simon issued Feb. 9, 1971,
3,691,047 to Ross et al issued Sept. 12, 1972, and
3,753,887 to Kedem et al issued Aug. 21, 1973.

The principle advantage of the ion-selective "barrel" electrodes, in addition to their high specificity is that if certain rigid conditioning procedures are applied between measurements, the electrode can be used repeatedly for measuring the concentration of the same ion in different solutions.

The major shortcomings of some conventional ion-selective electrodes include:

(1) cost: generally a single electrode costs several hundred dollars;
(2) fragility: the body and the membrane of glass electrodes are fragile; and
(3) reproducibility: even with the most carefully preformed conditioning procedures, after the first use of the electrode to determine the ionic activity of unconditioned fluids such as body fluids, the exact composition of the electrode membrane (glass or polymeric) is unknown due to the potential for contamination by earlier test solutions, and for this reason the results are often suspect.

In an attempt to solve some of the foregoing problems, Cattrall, R. W., and Freiser, H., Anal. Chem., 43, 1905 (1971), and James, H., Carmack, G., and Freiser, H., Anal. Chem., 44, 856 (1972), described calcium ion-selective "coated wire" electrodes comprising a platinum wire coated with a layer of a polyvinyl chloride solution of, for example, calcium didodecylphosphate (see also British Pat. No. 1,375,785 published Nov. 27, 1974). These authors make no mention of the use of an internal reference electrode or an internal reference solution and, in fact, specifically exclude these components. These electrodes are evaluated in Stworzewicz, T., Cyapkiewicz, J., and Lesko, M., "Selectivity of Coated Wire and Liquid Ion-Selective Electrodes" at the Symposium on Ion-Selective Electrodes at Mútrafüred, Hungary, October, 1972 (Proceedings reported in *Ion-Selective Electrodes*, edited by Pungor, E., Budapest, 1973, at pp. 259–267). The electrodes exhibit significant drift in electrical potential which requires frequent restandardization and hence makes their commercial use difficult.

Other known ion-selective electrodes are the reference and hydrogen ion-selective electrodes described in U.S. Pat. Nos. 3,833,495 issued Sept. 3, 1974 and 3,671,414 issued June 20, 1972, both to W. T. Grubb. These electrodes use a silver-silver halide reference electrode immersed in a thickened reference solution of a suitable "solvent medium," for example agar, carboxymethyl cellulose, polyvinyl alcohol, etc., and an ionic salt, e.g., KCl, in a shrinkable tube structure open at one end to the solution to be tested. In use, the reference solution contacts the solution under test directly with no intervening ion-selective membrane. The reference solution contains substantial quantities of water as evidenced by the fact that the recommended procedure for preparing the electrode involves injecting the electrolyte into the structure using a syringe.

French Patent Publication No. 2,158,905 published June 15, 1973, describes an ion-selective electrode which utilizes as the internal reference electrolyte solution a solution of a suitable salt (e.g., KCl) in a hydrated methylcellulose gel or, alternatively, a hydrophobic polystyrene ion-exchange resin overcoated with an ion-selective membrane comprising, for example, an organo polysiloxane or polycarbonate binder having a suitable ion carrier, for example, valinomycin dissolved or dispersed therein. The internal reference electrode described in this element comprises a metal wire (e.g., Ag) having a controlled coating of salt (e.g., AgCl) thereon. Whichever of the two alternative reference electrolyte materials is used (i.e., the gel or the ion-exchange resin), it is "hydrated" prior to application of the overlying ion-selective membrane.

In the case of hydrophobic ion-exchange materials prepared as described in U.S. Pat. No. 3,134,697 to Niedrach which is cited in French Pat. No. 2,158,905 as disclosing the preparation of such materials, the water content of these ion exchangers is between 15 and 50 percent. As is recognized by the skilled artisan, this water of hydration can be removed from such ion-exchange materials only with great difficulty.

U.S. Pat. No. 3,730,868 to Niedrach issued May 1, 1973, describes a carbon dioxide-sensitive electrode which uses a silver/silver halide internal reference electrode and a quinhydrone electrode as a pH sensor to detect changes in pH induced by $CO_2$ which penetrates an overcoated carbon dioxide-permeable membrane. There is no suggestion in this patent that useful electrodes can be obtained by overcoating this redox reference electrode directly with an ion-selective membrane to obtain an ion-selective electrode. Rather, an ion-exchange resin is used as an electrolyte solution to quantify variations in $CO_2$ concentration as permitted by the $CO_2$-permeable membrane. The electrode is therefore similar to those described in French Pat. No. 2,158,905, except that in one aspect a solid quinhydrone electrode is used as a pH sensor.

U.S. Pat. No. 3,856,649 issued Dec. 24, 1974, to Genshaw et al and a paper by the same authors entitled "Miniature Solid State Potassium Electrode for Serum Analysis", Analytical Chemistry, 45, pp. 1782–84 (1973), describe a solid state ion-selective electrode for potassium ion detection, which electrode comprises, on a wire, an electrically conductive inner element with a salt disposed on a surface portion thereof having as a cation, a cationic form of the inner element and also having an anion, a solid hydrophilic layer in intimate contact with the salt and including a water-soluble salt of the anion and a hydrophobic layer in intimate contact with the hydrophilic layer whereby the hydrophilic layer is shielded from contact with the ion-containing aqueous solution under test when the electrode is immersed therein. The patent refers to the importance of maintaining the electrode in a "hydrated" state during the course of manufacture and states at column 3, lines 27–29, "This hydrated state is considered important to the proper functioning of the electrode of this invention."

Although the Genshaw et al patent makes no specific and clear reference to it, the publication clearly states, and applicants have found in their evaluations of such electrodes, as demonstrated in the examples below, that, if accurate and reproducible results are to be obtained, electrodes of this type must be hydrated prior to use if stored dry (i.e., under ambient conditions, RH 40–50%) for extended periods after manufacture. Such hydration requires that the electrodes be stored in an aqueous solution or preconditioned in an aqueous solution prior to use in an ion-activity-determining operation. Failure to use such preconditioning or storage techniques will result in the generation of non-Nernstian responses which exhibit substantial random drift as described hereinafter, at least until such time as the electrode is hydrated by the sample solution. Furthermore, if the electrode is used in a "dry" or unpreconditioned state to quantify ions in a small sample of liquid (on the order of less than about 100 $\mu$l), the absorption of the substantial amounts of water which are necessary to bring the wire electrode to equilibration may result in a substantial change in the actual ion concentration before a reproducible potentiometric reading can be obtained.

Thus, although the "solid-state" electrodes described by Genshaw et al offer substantial advantages of size and the quantity of sample required for measurement, as compared with electrodes of the prior art, they retain one very significant shortcoming; namely, they must generally be either stored "wet" or hydrated (i.e., preconditioned) for some period prior to use.

Israeli Pat. No. 35,473 entitled "Ion-Specific Measuring Electrodes" describes an ion-selective electrode comprising an ion-selective membrane in conducting contact with a "conductive solid material," namely graphite, (particulate or solid) which in turn contacts a wire lead for the electrode. No reference solution or redox couple is described or suggested.

U.S. Pat. Nos. 3,649,506 and 3,718,569 issued Oct. 14, 1969 and Feb. 27, 1973 respectively "solid-state" glass electrodes in which a conductor having a surface layer of an electrochemically active metal is coated with a first coating of a mixture of a glass and a halide of the active metal and a second outer coating of non-sensitive glass. Presumably such electrodes require the same preconditioning techniques as conventional glass electrodes.

U.S. Pat. No. 3,900,382 issued Aug. 19, 1975 describes a miniaturized electrochemical electrode which functions as both an oxygen or carbon dioxide electrode and an ion-selective electrode. At Column 2, lines 43–53 it is suggested that the various layers could be applied by dipping the metal wire core of the electrode in various organic solutions after which each solution solvent was evaporated. Quite obviously this description cannot apply to the "electrolyte layer" designated 17 which comprises a solution of sodium bicarbonate and sodium chloride with a thickening agent. Such a layer could not be provided from an "organic solution" and hence the suggestion as to manufacture is inapplicable. Furthermore, at Column 4, lines 49–58 the electrolyte is explicitly described as an aqueous solution.

SUMMARY OF THE INVENTION

Figure 1:
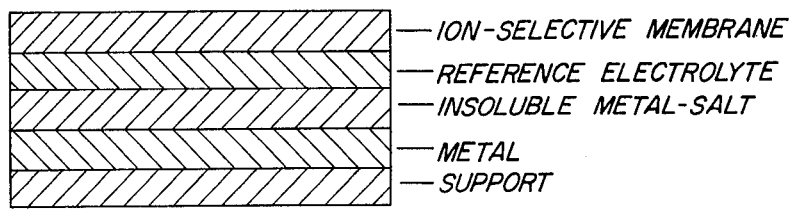
FIGS. 1 and 2 are cross-sectional views of ion-selective electrodes as described herein.

According to the present invention, there is provided a dry-operative ion-selective eletrode comprising:

(a) a dried internal reference electrode, and (b) in contact with the reference electrode, a hydrophobic ion-selective membrane.

The ion-selective electrodes described herein require no preconditioning prior to use in an ion-sensing operation.

The reference electrode may comprise either a metal metal-salt reference half-cell or a dried single- or multiple-layer redox couple reference electrode which is similarly wetted upon application of an aqueous sample as described hereinafter. The term "dried" as used herein is defined below.

According to a further preferred embodiment, the hydrophobic membrane includes an ion carrier dissolved in a suitable carrier solvent dispersed in a hydrophobic binder. A most preferred embodiment provides for electrodes of the type described which provide a substantially planar surface for contacting with a sample for testing and comprise a hydrophobic membrane of predetermined uniform thickness in regions intended for contact with a sample for analysis. The electrode optionally includes a support. A novel technique for making measurements of ion concentration by reading the electrode prior to substantial hydration thereof is also described.

The novel ion-selective electrode of the present invention, which is designed for use in the potentiometric analysis of liquids, is simple in structure, easily manufactured at a reasonable cost and therefore disposable, and highly accurate due to its economically feasible single-use capability which insures the integrity of the ion-selective membrane for each new measurement. As will be described in somewhat greater detail below, the electrode can be prepared in a variety of formats and geometries.

For a complete understanding of the invention described herein it is necessary to have an understanding of the phenomenon of electrode drift. As is well known to those skilled in the art, electrode drift is the variation in the potential sensed by an ion-selective electrode in contact with an ion-containing solution over a period of time.

Electrode drift is apparently due to a number of factors such as permeation of the ion-selective membrane by test solution solvent (generally water) with the passage of time, variations in ion concentration in the test solution in the region of the solution proximate the electrode, which variation is caused by the aforementioned solvent permeation, etc.

All ion-selective electrodes demonstrate some drift, however, the phenomenon is minimized in conventional electrodes by preconditioning the electrode to bring the electrode to a steady state approximating that expected to be encountered in a testing situation. In this fashion the user diminishes the factors which cause drift and consequently reduces drift in the testing situation. One might expect, therefore, that the use of a totally "unconditioned" ion-selective electrode would result in severe drift of potentially catastrophic proportions which would prohibit such use of the ion-selective electrode until the equilibrium state usually achieved by preconditioning had been reached in the test situation. Quite unexpectedly, it has now been discovered that ion-selective electrodes can be prepared which can be used without preconditioning of any sort and that the drift exhibited by these electrodes, although sometimes substantial, can be calibrated to provide accurate and reproducible determinations of the concentration of specific ions in test solutions. The features which impart this unusual performance capability to the electrodes of the present invention as well as the techniques for their manufacture and use will be elaborated hereinafter.

As used herein, the term "dry-operative" describes an ion-selective electrode which provides reproducible potentiometric determination of ionic activity which can be related to the ion concentration of aqueous test solutions with no requirement for "wet" storage (i.e., keeping in an aqueous solution) or preconditioning (i.e., soaking in a salt solution) prior to use. Essentially, what this means is that a "dry-operative" electrode produces accurate and reproducible determinations of potential which can be calibrated and thereby related via ionic activity to ionic concentration in an aqueous test solution without having first to be substantially hydrated or brought to the aforementioned equilibrium state. Many of the electrodes described herein perform in this manner even when used immediately after storage at 20% RH. The practical application of this definition will be made more apparent from the discussion and examples which follow.

The term "thin" when used in reference to individual layers of preferred embodiments of the electrodes of the present invention describes individual electrode layers having a maximum thickness of about 50 mils. Preferably, such "thin" layers are on the order of less than about 10 mils in thickness. Most preferred are layers on the order of less than about 2 mils.

The term "uniform" when used herein in reference to the thickness of the ion-selective membrane of a "dry-operative" electrode describes a predetermined thickness tolerance in regions of the layer intended for contact with a sample for analysis. This tolerance is met if the drift exhibited by the electrode incorporating such a layer can be calibrated, i.e., can provide reproducible determinations of potential related to concentration by calibration within an error tolerance acceptable for the particular measurement without preconditioning or permitting the electrode to reside in the test solution for a period sufficient to achieve conditioning by the test solution. Electrodes which do not possess "uniform" thicknesses will exhibit a random drift which cannot be calibrated to provide results which are directly related to ionic concentration. Uniformity of thickness is exhibited by dry operativeness will generally call for a maximum variation in the thickness of the membrane of at most about 20% in regions thereof intended for contact with a sample for analysis.

The term "dried" when used in reference to layers of electrodes described herein refers to a physical state of such layers brought about by subjecting, in manufacture, the layer to drying conditions, i.e., conditions for temperature, reduced vapor pressure or whatever, adequate to accomplish removal of sufficient solvent or dispersing medium as to render the layer non-tacky, as this term is commonly interpreted in the coating arts, prior to the application of any overlying layer(s). This drying to drive off solvent or dispersing medium is a major factor imparting the "dry-operative" capability to the electrodes of the present invention. Although the mechanism of this phenomenon is not fully understood, and applicants do not wish to be bound by any theory of operation for their electrodes, it appears that the shrinking which the "dried" layer undergoes with loss of liquid in drying assures intimate contact between the "dried" layer and the contiguous superposed ion-selective membrane even under relatively harsh storage conditions of very low relative humidity, i.e., 20% RH or less. In this regard, it is generally desirable to relate the relative humidity of drying conditions in manufacture to the expected conditions of use as this will provide an optimized state of hydration for the ion-selective electrode. This relation is, however, not necessary to obtain useful electrodes. More specific conditions and requirements for certain dried layers of the electrodes of this invention will be stated hereinafter.

As described herein, such "dried" layers generally demonstrate minimal if any measurable conductivity and in the case where gelatin is used as the binder for the electrolyte layer as described hereinafter contain less than about 15% by weight of water an in some cases even as low as about 12–13% by weight of water.

Typical of the "dried" layers described herein are those obtained by forming layers under the following conditions:

(A) A solution comprising from about 5 to about 9% by weight gelatin is coated at a level of about 64 g/m$^2$ and dried under the following conditions:
  (1) chill set for about six minutes at 4° C. and a dew point of 50% RH; and
  (2) dry for about four minutes at 21° C. and 50% RH;

(B) Solutions of from about 5 to about 9% of polyvinyl alcohol and poly(2-hydroxyethyl acrylate) are coated at a level of about 64 g/m$^2$ and dried under the following conditions:
  (1) heat set for about six minutes at 55° C. and 50% RH; and
  (2) dried for about four minutes at 35° C. and 50% RH. These drying conditions are not required to obtain layers of the type described herein, however, they are typical of conditions which may be used to obtain dried layers of the type described herein using a variety of polymer matrices suitable as the binder for the reference electrolyte layer. Such layers demonstrate the "dryness" required of the reference electrode layer prior to application of the ion-selective membrane.

The electrodes described herein are generally capable of producing concentration determinations which demonstrate a coefficient of variation of less than about 10%. Electrodes prepared in accordance with preferred embodiments hereof demonstrate coefficients of variation of less than about 3% and in certain highly preferred embodiments, coefficients of variation of below about 2% have been achieved.

DESCRIPTION OF THE PREFERRED EMBODIMENTS

As described hereinabove, previous so-called "solid-state" electrodes required the incorporation as an internal electrolyte of either an aqueous salt solution, a hydrated salt, or a layer of salt impregnated glass to achieve operative measurements of ionic concentration. All such electrodes require preconditioning prior to use in an ion-sensing operation. It has now surprisingly been discovered that electrodes having a "dried" internal electrolyte and ion-selective membrane of predetermined uniform thickness can be used to achieve acceptable levels of precision and accuracy in potentiometric ionic determinations similar to those until now achievable with electrodes which required preconditioning, at ambient conditions without any substantial preconditioning or wet storage. The ion-selective electrodes of the present invention present a dry, solid appearance and require only a drop (i.e., below about 50 μl and preferably about 10 μl) of solution to produce an accurate measurement. They require no preconditioning prior to use, measurements can generally be made in less than five minutes and because of their low cost they can be discarded after a single measurement, thereby avoiding contamination due to prior use thereby insuring integrity of the ion-selective membrane for each new measurement. Furthermore, a novel technique for using the ion-selective electrodes of this invention permits rapid yet accurate quantitative ionic determinations.

Although the layers described hereinafter are generally referred to as being "coated" one over another, it should be understood that the term "coating" is meant to include laminating or otherwise depositing the various strata one over another, as well as actually coating using conventional coating, dipping or extrusion techniques to achieve layering of the various strata.

The dry-operative ion-selective electrodes of the present invention comprise:
  (a) a dried, internal reference element,
  (b) in contact with the reference electrode, a hydrophobic ion-selective membrane (of predetermined uniform thickness in areas thereof intended for contact with a test solution), and
  (c) an optional support.

REFERENCE ELECTRODE

As with any ion-selective electrode useful in the determination of ionic activity and consequently ionic concentration in solution, the electrodes of the present invention have an internal reference electrode which exhibits a reproducible reference potential against which the potential occurring at the interface between the ion-selective electrode and the solution under test is measured.

Figure 2:
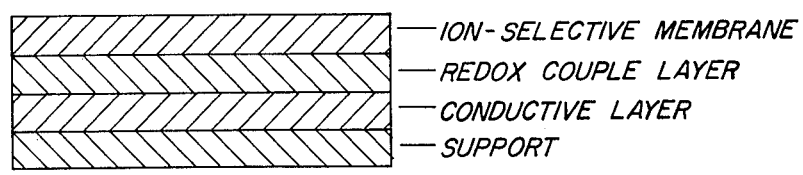

According to the present invention, the reference electrode may be of two distinct types, both of which exhibit the required fixed potential necessary to achieve useful results. The useful reference electrodes are:
  (1) metal/metal-salt electrodes (see FIG. 1), and
  (2) redox couple electrodes (see FIG. 2).

METAL/METAL-SALT ELECTRODES

A commonly used internal reference electrode comprises a metal in contact with an insoluble salt of the metal which is in turn in contact with an electrolyte, i.e., a solution containing the anion of the salt. An example of a very commonly used such element is represented as Ag/AgCl/"XMCl$^-$" (XMCl$^-$ indicating a solution of known Cl$^-$ concentration) and comprises a silver wire having a coating of silver chloride applied thereto dipping into an aqueous solution of known chloride concentration. A calomel electrode, Hg/Hg$_2$Cl$_2$/Cl$^-$, is another example of this type of electrode. This type of internal reference electrode is used in most barrel electrodes and in the known, so-called "solid-state" (as referred to in Genshaw) electrodes. In known "solid-state" electrodes, the electrolyte solution comprises a hydrated gel, hydrated PVA, hydrophobic ion-exchange resin, etc., as described above. The reference electrodes of the present invention are dried during manufacture and, unexpectedly, do not require conditioning prior to use.

According to the present invention, the metal/metal-salt reference electrode comprises a conductive layer of a metal in conducting contact with a layer of a salt of the metal as used in known electrodes and a dried electrolyte layer in contact with the metal-salt layer.

The conductive metal layer may comprise any suitable conductive metal of the well known types which have been used in such electrodes, and which is compatible with the structure, particularly the formats described herein. Particularly useful conductive metal layers include suitably thin layers of silver, nickel, and platinum.

The salt layer in contact with the conductive layer may comprise substantially any insoluble salt of the metal of the conductive layer which establishes a fixed interfacial potential with the metal of the conductive layer. Such layers, which are well known and thoroughly described in the aforementioned patents and publications, generally comprise a salt of the metal which is a product of the oxidation of the metal, as, for example, AgCl, Hg$_2$Cl$_2$, etc. A highly preferred embodiment of the present invention utilizes the aforementioned well known Ag/Ag$_n$X (wherein X=S$^-$, Cl$^-$, Br$^-$ or I$^-$ and n=1 or 2) interface to establish the potential of the reference electrode. Electrode elements of this type can be prepared using a number of well known techniques which include, by way of example, dipping a layer of silver as a wire, foil or supported thin layer into a solution of molten silver halide. According to a preferred embodiment of the present invention, the silver-silver halide couple is produced by vacuum depositing silver onto a suitable support of the type described below, preferably an insulating film, and then chemically converting a surface stratum of the silver layer to silver halide. Generally, techniques for chemically converting metal to metal halide involve exposure or contact of the surface of the metal, in this case silver, with a solution of a salt of the halide to be formed in the presence of an oxidant for a period and at a temperature sufficient to cause the desired conversion. Typical conditions for this sort of chemical conversion are well known, and examples of simple and preferred techniques are shown in the examples below. Other useful techniques for preparing each electrodes are described in U.S. Pat. Nos. 3,591,482 to Neff et al issued July 6, 1971, 3,502,560 to Wise issued Mar. 24, 1970, and 3,806,439 to Light et al issued Apr. 23, 1974. Although the teachings of all of these references are directed primarily to the preparation of wire electrodes, the application of ordinary engineering skill will render their application to the manufacture of electrodes constructed on thin films of polymeric support apparent. Alternatively, a discrete layer of silver halide may be coated over the silver layer so long as appropriate contact between the silver and silver halide is maintained.

Although it is possible to obtain the metal/metal-salt interface with substantially any ratio of metal layer to salt layer thickness, in a preferred embodiment which assures a sufficiently dense layer of metal salt it is preferred that the insoluble metal-salt layer have a thickness equal to at least 10% of the overall thickness of the conductive metal layer. According to a preferred embodiment of the present invention wherein a surface layer of a vacuum-deposited silver layer is converted to a suitable salt, from about 10 to about 20% of the thickness of the silver layer is converted to silver salt using chemical conversion techniques.

The second member of the metal/metal-salt reference electrodes of the present invention comprises the electrolyte layer. According to a preferred embodiment of the present invention, the electrolyte layer is a dried hydrophilic layer.

The dried electrolyte solution of the present invention comprises a hydrophilic binder having a salt in solid solution therewith. According to a preferred embodiment, the anion of the salt is common to the salt of the metal-salt layer and at least a portion of the cation of said salt comprises the ion which the electrode is designed to detect.

"Dried" hydrophilic electrolyte solutions as described herein are specifically distinguished from the hydrated polyvinyl alcohol layers described in U.S. Pat. No. 3,856,649. The "dried" reference solution of this invention comprises the dried residue of a solution of a salt and a suitable hydrophilic polymeric binder in a solvent for the polymer and the salt. This distinction will be made more apparent by the discussions of making and using the electrodes of the instant invention which are presented hereinafter.

The binder for the "dried" reference electrolyte solution may comprise any hydrophilic material suitable for the formation of continuous, coherent, cohesive layers compatible with the salt of the electrolyte layer and, if formed by coating, a solvent system for both the ionic salt and the polymeric binder. Preferred materials of this type are hydrophilic natural and synthetic polymeric film-forming materials such as polyvinyl alcohol, gelatin, agarose, deionized gelatin, polyacrylamide, polyvinyl pyrrolidone, hydroxyethyl acrylate, hydroxyethyl methacrylate, polyacrylic acid, etc. Specifically preferred from among these materials are the hydrophilic colloids such as gelatin (especially deionized gelatin), agarose, polyvinyl alcohol and hydroxyethyl acrylate.

The ionic salt which is dissolved in the polymeric binder solution will be determined by the composition of the metal/metal-salt portion thereof. For example, in a potassium selective electrode which uses AgCl as the insoluble metal salt, potassium chloride is a logical choice although sodium chloride, etc. may also be used. For sodium ion determinations in a similar configuration, sodium chloride would be useful, etc. Thus, the salt will generally be a water-soluble salt having a cation selected from ammonium, alkali metals and alkaline earth metals, mixtures of same or any other suitable cation to which the electrode responds, and as anion a halogen or sulfur depending upon the composition of the metal-salt layer. Conductive metal salts of these anions are commonly insoluble.

Appropriate solvents for the polymeric binder and ionic salt will depend largely on the nature of the polymer and the salt. Generally, polar solvents suitable for dissolving the salt and the polymer are satisfactory. Thus, water is a preferred solvent for layers of hydrophilic materials such as polyvinyl alcohol and gelatin.

Since the thickness of the "dried" electrolyte layer will to some extent determine the response characteristics of the electrode, it is generally desirable to maintain the "dried" layer rather thin. Layers having dry thicknesses on the order of from about 0.1 to about 0.5 mil have been found useful. A preferred thickness is about 0.2 mil. Of course, where electrode response characteristics are not critical, the thickness of the layer may vary over a wide range and only the application of sound engineering skills and the use requirements of the finished electrode will determine its limits.

The concentration of ionic salt in the "dried electrolyte layer" may also be varied widely, depending upon response time desired, etc. and especially the level or amount of polymer used. In the preferred embodiments described herein wherein the binder level ranges from about 2.4 g/m$^2$ to about 10 g/m$^2$, the concentration of the salt ranges from about 1.40 to about 2.5 g/m$^2$. Below this level, electrode drift may be a problem as elaborated below, and above this level coating of the layer becomes somewhat difficult. Of course, where drift is not critical, layers of substantially greater thickness are used, or layers are prepared by some technique other than coating, concentrations of salt outside these ranges may be similarly useful. Generally, salt concentrations of from about 20 to about 40 percent by weight total solids in the layer are preferred.

When the reference electrode is prepared by coating the various layers one over another, it may be desirable to include surfactants or coating aids in the coating solution during manufacture. Such materials should preferably be nonionic and, whatever their composition, they should not include ions which introduce variants into the fixed potential differences existing at the various electrode layer interfaces and are most preferably potentiometrically inert. Of course, where additives which do introduce variants into the potentials exhibited at the various interfaces are used, it is possible to compensate for these differences. Among the materials found useful for this purpose are natural surfactants such as saponin and synthetic materials such as poly(ethylene glycol) and a material commercially available from Olin Mathieson Company under the tradename Surfactant 10G. Other useful materials of this type include octyl phenoxy polyethoxy ethanols such as TX-100, TX-405, etc. commercially available from Rohm & Haas Company.

In an alternative embodiment useful metal/metal salt (specifically Ag/AgX) reference electrode elements can be prepared using techniques common to the manufacture of photographic film.

According to such procedures either or both of the metal (i.e. silver) and metal salt (i.e. silver halide) are prepared by coating suitable silver halide photographic emulsions and processing as required. For example, a useful silver halide layer can be prepared applying to a vacuum deposited silver layer by coating a conventional fine grain silver chloride-gelatin emulsion at coverages of from 0.054 to 0.54 g/m² of gelatin and 1.16 to 1.83 g/m² of silver as silver chloride. In evaluations with standard chloride solutions, such electrodes demomstrated substantially Nernstian response (i.e. slopes of about 59 mv/dec).

Useful silver layers which can be overcoated with silver haide layers as just described have been prepared by coating a poly(ethylene terephthalate) support with a layer of fine grain silver chloride, gelatin emulsion at a coverage of 2.02 g/m² of silver as silver chloride and 95 mg/m² of gelatin using conventional photographic film manufacturing techniques. The silver chloride layer was then developed for five minutes in a standard black and white developer solution known as Kodak Developer D-19 at room temperature and under white light conditions. After thorough washing and drying this layer was overcoated with a silver chloride emulsion as just described. Samples of this electrode responded acceptably to standard chloride ion solutions.

Useful electrodes have also been obtained by coating the silver chloride emulsion over evaporated layers of gold, copper and nickel and using fine grain silver bromide emulsions to prepare the metal salt layer.

OXIDATION-REDUCTION ELECTRODES

The second type of internal reference electrode useful in the successful practice of the present invention is the so-called oxidation-reduction electrode (hereinafter redox electrode). Redox electrodes have been described and generally include an inert metal wire dipping into a solution containing two different oxidation states of a chemical species. An example of such an electrode comprises a platinum wire dipping into a solution containing ferrous and ferric ions. Such a cell is abbreviated Pt/Fe$^{++}$, Fe$^{+++}$. The electrode reaction is Fe$^{+++}$ + e$^-$ ⇌ Fe$^{++}$. Redox electrodes can also be made with organic molecules that can exist in two different oxidation states. The most widely used of this type is the so-called quinhydrone electrode in which the redox system is:

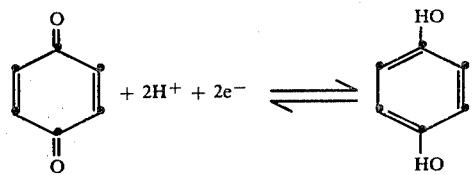

and the cell is represented as:

Pt/QH$_2$, Q, H$^+$

Redox electrodes of this type can also be prepared in a "solid-state" format to provide the internal reference element of the composite ion-selective electrodes of the present invention. Alternatively such electrode may be used as external reference electrodes in the overall determination of ion concentrations in solution in place of conventional external reference electrodes such as the saturated calomel (i.e., Hg/HgCl$_2$) electrode. U.S. Pat. No. 3,730,868 also describes such a redox electrode.

The redox electrode of the present invention comprises:

(a) a solid, electrically conductive layer in contact with
(b) a redox couple. The redox couple may be dissolved or dispersed in the electrically conductive layer or be provided as a discrete solid layer comprising the redox couple dissolved or dispersed in a suitable binder and in conducting contact with the conductive layer.

THE CONDUCTIVE LAYER

The conductive layer of the redox reference electrode comprises an electrically conductive material or conductor (as this term is conventionally understood in the art). It will be appreciated that the conductive material should not interact with the redox composition except in the desired and controlled electrochemical fashion required for operation of the electrode, i.e., to establish a reproducible reference potential. Useful results have been obtained with such inert conductors as carbon, platinum, gold and nickel. So long as the conductor is selected so that no unstable electrochemical or other undesired interaction with the redox couple is observed, the choice is not critical. A particularly useful conductor is carbon (in particular, particulate carbon), as will be shown in the examples and described in greater detail below.

In certain embodiments, as in the case of carbon where the inert conductor may be in the form of discrete conductive particles, it may be necessary that such particles be maintained in electrically conductive contact in a solid layer by means of some binder or matrix. The binder may comprise any material which permits intimate particle-to-particle contact and conductive contact between the conductor and the redox couple as described hereinafter. Generally, such binders comprise relatively low concentrations of hydrophilic polymers such as gelatin, polyvinyl alcohol and polyvinyl pyrrolidone. It is, however, possible to use hydrophobic polymers such as silicone rubber for the binder.

Whatever the binder used, the ratio of conductor to binder must be sufficiently high that the resistance of the layer is low enough to insure adequate electrical conductivity. Such resistances are obtainable with weight ratios of conductor to binder of between about 1:1 and about 3:2.

THE REDOX COUPLE COMPOSITION:

The redox couple composition comprises the soluble redox couple and whatever other means are required to maintain the composition in a solid form. This other means generally comprises a matrix or binder of one sort or another which contains the redox couple as a solid solution or dispersion.

The redox couples of the present invention, as alluded to above, comprise pairs of the same chemical species (usually ions) in differing oxidation states.

The formal potential of the reference electrode of the present invention, i.e., the electrical potential of the redox couple at equal concentrations of its reduced and oxidized components at some defined finite value of ionic strength, is determined by:

(1) the redox couple chosen and
(2) the ratio of activities of oxidized to reduced components. According to a preferred embodiment of the present invention, the ratio of the oxidized to the reduced component (i.e., the molar ratio of material in one oxidation state to material in the other oxidation state) is about unity (1), since, the redox buffer capacity is largest at this ratio. Of course, depending upon the type of measurement to be made using the electrodes described herein, this ratio may be varied quite broadly.

When the electrode is wetted with a sample solution, the redox couple must be capable of establishing a reproducible interface with the conductive layer to establish a reproducible and reproducible potential; i.e., the redox couple must be capable of exchanging electrons with the conductive layer in a constant fashion when the potentiometric circuit is completed. It is important that the conductive layer and the redox couple together poise the potential of the redox chemistry in a fast electrochemical exchange reaction between the redox couple and the conductor. It is this capability to establish a reproducible potential which is referred to herein as the "compatibility" of the redox couple with the conductive layer. A redox couple which readily establishes such a fixed potential with a given conductor is said to be "compatible" therewith.

According to a preferred embodiment, it is, of course, desirable that in order for the electrode to possess an extended shelf-life capability, the oxidized and reduced forms of the couple should be stable for the desired shelf-life.

Redox couples which have been found particularly useful in the successful practice of the present invention include ferric/ferrous ion couples such as $Fe(CN)_6^{-3}/Fe(CN)_6^{-4}$ and cobaltic/cobaltous couples such as $Co(terpyridyl)_2^{+3}/Co(terpyridyl)_2^{+2}$ wherein terpyridyl is 2,6-di-2'-pyridylpyridine.

Any redox couple capable of exchanging electrons with a compatible conductive layer and sufficiently stable against aerial oxidation as to provide a useful shelf-life is useful in the successful practice of the invention.

Although some redox couples may be applied as a solid layer directly to the conductive layer without a matrix or binder, in view of the high solubility of many of the useful redox couples and the difficulty with which materials of this type are applied to the conductive layer in their solid form (i.e., as crystals, etc.), it is generally desirable to apply the redox couple as a dispersion or solution in a suitably porous or water permeable binder or matrix.

The preferred water permeable matrixes for the redox couple comprise a hydrophilic colloid such as gelatin, polyvinyl alcohol, polyacrylamide, polyvinyl pyrrolidone, etc., which colloid is most preferably:

(a) sufficiently hardened or cross-linked to prevent substantial dissolution thereof by water which may contact it, and
(b) sufficiently hydrophilic to permit electrolytic contact with the conductive metal layer.

As alluded to hereinabove, it is also possible to use highly porous layers of hydrophobic material wettable by virtue of their porosity and permitting conducting contact between particulate members of the redox couple also by reason of this porosity. Thus, water permeable, highly porous layers (i.e., comprising over about 60% and preferably over about 75% void volume) of such hydrophobic materials as cellulose acetate or poly(n-butylmethacrylate-co-2-acrylamido-2-methylpropane sulfonic acid-co-2-acetoacetoxyethyl methacrylate) can be used as the binder or matrix for the redox couple.

Although the redox reference electrodes are generally prepared in a two-layer configuration (i.e., a solid layer of inert conductor in conducting contact with a superimposed solid dried redox couple layer), it has also been found that both the inert conductor and the redox couple may be incorporated into a single layer to provide a useful electrode. In this configuration, it is preferred to use a hydrophilic matrix of the type described above in connection with the redox couple layer for the combined layer; however, hydrophobic binders are also useful. Embodiments of single-layer reference electrodes are described in the Examples below. The techniques for their preparation and use are identical to those of the two-layer or double-layer electrodes described herein.

It is specifically noted at this point that glass internal reference electrodes are not considered to be within the definition of "dried internal reference" electrodes described hereinabove. The term "glass" is meant to include conventional inorganic glasses, for example, of the type described in U.S. Pat. No. 3,149,506.

ION-SELECTIVE MEMBRANE

Whichever of the foregoing internal reference electrodes is used, the ion-selective membrane is laminated, coated or otherwise applied directly thereover. It is important to the successful practice of the present invention that the ion-selective membrane be applied at the time of manufacture so as to assure intimate and uniform contact with the surface of the reference electrode contiguous with the ion-selective membrane at least in those areas intended for contact with a test solution to obtain a "dry-operative" electrode. Such intimate uniform contact of the ion-selective membrane with the dried internal reference electrode at the time of manufacture produces a reference electrode-ion-selective membrane interface which will respond almost immediately upon contact of the ion-selective membrane with a test solution.

Among the patents and publications which describe ion-selective membranes of the type useful in the instant invention, the contents of all of which are incorporated herein by reference to the extent that they are pertinent, are:

U.S. Pat. No. 3,562,129 to Simon issued Feb. 9, 1971;
U.S. Pat. No. 3,753,887 to Kedem et al issued Aug. 21, 1973;
U.S. Pat. No. 3,856,649 to Genshaw et al issued Dec. 24, 1974;
British Pat. No. 1,375,446 issued Nov. 27, 1974;
German OLS 2,251,287 issued Apr. 26, 1973;
Morf, W. E., Kohr, G., and Simon, W., "Reduction of the Anion Interference in Neutral Carrier Liquid-Membrane Electrodes Responsive to Cations", *Analytical Letters*, Vol. 7, No. 1, pp. 9–22 (1974);
Morf, W. E., Ammann, D., Pretsch, E., and Simon, W., "Carrier Antibiotics and Model Compounds as Components of Ion-Sensitive Electrodes", *Pure and Applied Chemistry*, Vol. 36, No. 4, pp. 421–39 (1973);
Ammann, D., Pretsch, E., and Simon, W., "Sodium Ion-Selective Electrode Based on a Neutral Carrier", *Analytical Letters*, Vol. 7, No. 1, pp. 23–32 (1974);
Cattrall, R. W., and Freiser, H., *Anal. Chem.*, 43, 1905 (1971); and
James, H., Carmack G., and Freiser, H., *Anal. Chem.*, 44, 856 (1972).

Membranes of this type which are well-known generally include an inert hydrophobic binder or matrix having dispersed therein an ion carrier or selector commonly referred to as an ionophore which imparts selectivity to the membrane dissolved in a carrier solvent to provide adequate ion mobility in the membrane. The carrier solvent generally also serves as a plasticizer for the membrane binder.

ION-SELECTIVE MEMBRANE BINDER

Binders for use in the ion-selective membrane of the instant invention include any of the hydrophobic natural or synthetic polymers capable of forming thin films of sufficient permeability to produce, in combination with the ionophores and ionophore solvent(s), apparent ionic mobility thereacross. Specifically, polyvinyl chloride, vinylidene chloride, acrylonitrile, polyurethanes (particularly aromatic polyurethanes), copolymers of polyvinyl chloride and polyvinylidene chloride, polyvinyl butyral, polyvinyl formal, polyvinylacetate, silicone elastomers, and copolymers of polyvinyl alcohol, cellulose esters, polycarbonates, carboxylated polymers of polyvinyl chloride and mixtures and copolymers of such materials have been found useful. Films of such materials which include the ionophores and carrier solvents may be prepared using conventional film coating or casting techniques and, as shown in the examples below, may be formed either by coating and film formation directly over the internal reference electrode or some suitable interlayer or by formation separately and lamination thereto.

ION CARRIER

The ion carrier used in the ion-selective membrane is generally a substance capable of selectively associating or binding to itself preferentially a desired specific alkali metal, alkaline earth, ammonium or other ions. The manner in which the ion becomes associated with the carrier is not fully understood but it is generally thought to be a steric trapping phenomenon complexing by coordination or ion exchange. Suitable ion carriers are more fully described below.

The selectivity of the electrode for a particular ion is due to the chemical nature of the ion carrier and, thus, the use of different chemical components as the ion carrier provides different membranes for use in ion-selective electrodes specific to different ions. Exemplary of such components are a large number of substances, some of them known to be antibiotics, which includes:

(1) valinomycin, a potassium-selective (over sodium), ion carrier that imparts to a membrane constructed in accordance with this invention a potassium ion selectivity of the order of $10^{-4}$, and an ammonium ion selectivity (over sodium) of the order of $10^{-2}$;
(2) cyclic polyethers of various constitution which make the membrane selective to lithium, rubidium, potassium, cesium or sodium; and
(3) other substances having ion selectivity similar to valinomycin such as other substances of the valinomycin group, tetralactones, macrolide actins (monactin, nonactin, dinactin, trinactin), the enniatin group (enniatin A, B), cyclohexadepsipeptides, gramicidine, nigericin, dianemycin, nystatin, monensin, esters of monensin (especially methyl monensin for sodium ion-selective membranes), antamanide, and alamethicin (cyclic polypeptides).

There can also be used either a single substance or mixtures of substances of the formula:

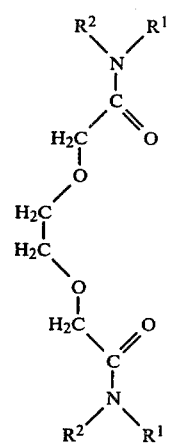

wherein:

I  $R^1$: —CH$_3$
   $R^2$: —(CH$_2$)n—COO—CH$_2$—CH$_3$
   wherein n = 1 or 10
II $R^1$: —CH$_3$
   $R^2$: —(CH$_2$)$_6$—CH$_3$
III $R^1 = R^2$: —CH$_2$—CH$_2$—CH$_3$
IV $R^1$: —CH$_2$—CH$_2$—CH$_3$
   $R^2$: —CH$_2$—C—(CH$_3$)$_3$
V  $R^1 = R^2$: —[phenyl]

VI 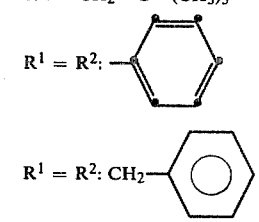

$R^1 = R^2$: CH$_2$—[phenyl]

Other useful ionophores include tetraryl borates (especially tetraphenyl boron) and quarternary ammonium salts. Compounds such as trifluoroacetyl-p-alkyl benzenes are described in U.S. Pat. No. 3,723,281 issued Mar. 27, 1973, as ionophores for HCO$_3^-$.

Compounds of the following structural formulas are also useful as ionophores:

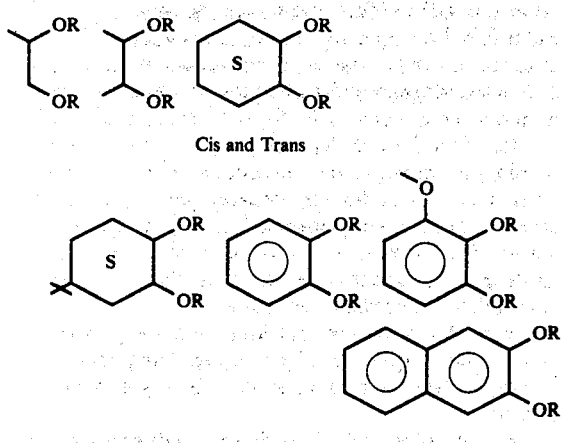

Cis and Trans wherein:
(a) $R = CH_2CON(CH_2CH_2CH_3)_2$

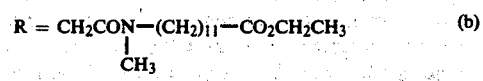 (b)

These materials are described by Amman, D., Bissig, R., Güuzzi, M., Pretsch, E., Simon W., Borowitz, I. J., Weiss, L., in Helv. Chim. Acta, 58, 1535 (1975).

Useful calcium ion selective electrodes can be prepared using antibiotic A-23187 as the ion carried and tris(2-ethyl hexyl) phosphate, tri(m-tolyl)phosphate, or dioctyl phenyl phosphonate as the carrier solvent. (See Pressman, B. C., Annual Review of Biochemistry, E. B. Snell, ed., Vol. 45, 1976, pp. 501–503).

Numerous other useful materials are described in the foregoing publications and patents, as well as other literature on this subject.

The concentration of ion carrier in the membrane will, of course, vary with the particular carried used, the ion undergoing analysis, the carrier solvent, etc. It has generally been found, however, that ion-carrier concentrations of below about 0.1 g/m² of membrane assuming the membrane thicknesses preferred herein result in marginal and generally undesirable responses. Ion-carrier concentrations of between about 0.3 and about 0.5 g/m² are preferred. The ion carrier can be incorporated at levels much higher than this; however, because of the cost of many of these materials, use of such levels is not economically sound.

ION CARRIER SOLVENT

The carrier solvent provides ion mobility in the membrane and, although the ion-transfer mechanism within such membranes is not completely understood, the presence of a carrier solvent is apparently necessary to obtain good ion transfer.

The carrier solvent must, of course, be compatible with the membrane binder and be a solvent for the carrier. In the structure of the present invention, two other characteristics are most desirable. One is that the carrier solvent be sufficiently hydrophilic to permit rapid wetting of the membrane by an aqueous sample applied thereto to permit ionic mobility across the interface between the sample and the membrane. Alternatively, the carrier must be rendered hydrophilic by the action of a suitable noninterfering surfactant which improves contact between the sample in contact with the membrane and the carrier.

The other highly desirable characteristic is that the carrier solvent be sufficiently insoluble in water that it does not migrate significantly into an aqueous sample contacted with the surface of the membrane as described hereinafter. Generally, an upper solubility limit in water would be about 4.0 g/l with a preferred limit lying below about 1 g/l. Within these limits, substantially any solvent for the ionophore which is also compatible with the binder may be used. As mentioned above, it is, of course, preferred that the solvent also be a plasticizer for the binder. It is also desirable that the ion carrier solvent be substantially non-volatile to provide extended shelf-life for the electrode. Among the useful solvents are phthalates, sebacates, aromatic and aliphatic ethers, phosphates, mixed aromatic aliphatic phosphates, adipates, and mixtures thereof. As shown in Example 8 below, specific useful carrier solvents include trimellitates, bromophenyl phenyl ether, dimethylphthalate, dibutylphthalate, dioctylphenylphosphonate, bis(2-ethylhexyl)phthalate, octyldiphenyl phosphate, tritolyl phosphate, tris(3-phenoxyphenyl) phosphate, tris(2-ethylhexyl) phosphate, and dibutyl sebacate. Particularly preferred among this class are bromophenyl phenyl ether and trimellitates for potassium electrodes using valinomycin as the carrier.

Specifically preferred from among the trimellitates are compounds of the formula

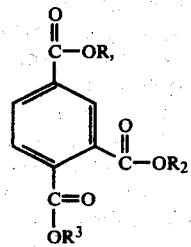

wherein $R_1$, $R_2$ and $R_3$ are alkyl groups of from 5 to 12 carbon atoms optionally such alkyl groups being the same or different.

When methyl monensin is used as the ionophore in a sodium ion-selective electrode, a preferred solvent is tris(3-phenoxyphenyl) phosphate.

A large number of other useful solvents are specified in the references mentioned above which describe the preparation of ion-selective membranes and any of these which permit assembly of electrodes of the type described herein may be used in the successful practice of the instant invention.

The concentration of carrier solvent in the membrane will also vary greatly with the components of a given membrane; however, weight ratios of carrier solvent to binder of between about 1:1 to about 5:2 provide useful membranes. The thickness of the membrane will affect electrode response as described in somewhat more detail below, and it is preferred to maintain the thickness of this layer below about 5 mils and preferably about 1 mil. As also described in greater detail below, the uniformity of thickness of the ion selective membrane plays an important role in the optimum utilization of electrodes of the type described herein. Thus, if maximum advantage in terms of storage capability and brevity of response time are to be obtained, the ion-selective membrane should be of relatively uniform thickness as defined above.

Quite clearly, the foregoing description of useful ion-selective membranes does not include ion-sensitive glasses which do not comprise a hydrophobic binder, ion carrier, and ion carrier solvent.

SUPPORT

According to preferred embodiments, the ion-selective electrodes of the present invention include a support which may be comprised of any material capable of bearing, either directly or by virtue of some intervening adhesion-improving layer, the other necessary portions of the electrode which are described in detail hereinafter. Thus, the support may comprise ceramic, wood, glass, metal, paper or cast, extruded or molded plastic or polymeric materials, etc. The composition of the support is relatively unimportant, so long as it is capable of carrying the overlying electrode components and it is inert; i.e., it does not interfere with the indicating potentials observed as, for example, by reacting with one of the overlying materials in an uncontrolled fashion. In the case of porous materials such as wood, paper or ceramics, it may be desirable to seal the pores before applying the overlying electrode components. The means of providing such a sealing are well known and no further discussion of the same is necessary here. Electrically insulating supports are preferred although, as described hereinafter, metallic conductive supports which serve multiple purposes are equally useful and may in fact simplify the structure of the electrode.

According to a highly preferred embodiment of the present invention, the support comprises a sheet or film of an insulating polymeric material. A variety of film-forming polymeric materials are well suited for this purpose, such as, for example, cellulose acetate, poly(ethylene terephthalate), polycarbonates, polystyrene, etc. The polymeric support may be of any suitable thickness typically from about 2 to about 20 mils. Similarly thin layers or surfaces of other materials mentioned above could be used. Methods for the formation of such layers are well known in the art.

In certain cases, a separate and distinct support need not be provided. Such a case occurs when one or more layers of the electrode demonstrate sufficient mechanical strength to support the remaining portions of the electrode. For example, when a metal-insoluble metal-salt electrode is used as the internal reference electrode as described below, the metal layer may be in the form of a self-supporting foil. The metal foil serves as the support, an integral portion of the internal reference electrode, as well as a contact for the electrode.

PREPARATION OF THE ELECTRODE

The solid-state electrodes of the prior art are commonly manufactured using a conductive wire as the starting material and dipping the wire sequentially into generally highly viscous solutions of the components of the individual finished electrode layers to construct a bulbous multilayer "solid-state" electrode. See, for example, U.S. Pat. No. 3,856,649. Alternatively, as shown in U.S. Pat. No. 3,649,506, individual layers of ion-selective glass are applied over the tip of a conductive wire. In either of these situations, the resulting ion-selective membrane is of relatively non-uniform thickness in those areas intended for contact with an aqueous solution whose ionic activity is to be determined.

There is a suggestion in U.S. Pat. No. 3,856,649 (col. 2, lines 1-3) that similar multilayer solid-state electrodes could be prepared in a sheet or web-form configuration as on a metallized film of a nonconducting support or a metal foil; however, there is no demonstration of such an electrode and certainly no appreciation of the unique and novel storage and use characteristics of carefully prepared electrodes of uniform layer structure which are described herein. Wire electrode configurations are within the scope of the present invention. However, when such electrodes are prepared, care must be exercised to reduce discrepancies in layer thickness (to within the tolerances described herein), etc., which might provide undesirable results in the novel measuring methods described hereinafter.

Electrodes of the present invention are prepared by coating, laminating or otherwise applying the various individual layers one over another in any conventional fashion.

Thus, a typical manufacturing procedure for a metal-insoluble metal-salt reference element electrode would involve chemically converting or otherwise applying a layer of an insoluble metal salt to a layer of a compatible conductive metal in the form of a coating on a nonconductive substrate or a metallic foil, overcoating the metal-salt layer with an electrolyte solution layer, drying the thus applied layer to remove solvent (see definition of "dried" hereinabove), and subsequently overcoating with a solution of the components of the ion-selective membrane and drying to provide a complete electrode. Alternatively, the layers can be laminated so long as intimate contact between layers is achieved and maintained, and uniformity of thickness of the ion-selective membrane is attained.

The particular drying conditions which must be applied to the internal reference electrode in the manufacture of any specific ion-selective electrode will, of course, vary greatly depending upon the composition of the electrode layers, particularly the binder used, the solvent or dispersing medium used to form the layer and these can be readily determined by the skilled artisan. Typical such conditions are described in the examples below for layers of the composition described therein.

Coating of the various electrode layers provides a uniquely simple yet efficient method for preparing electrodes as described herein. Using well known techniques, the various layers can be deposited under very carefully controlled conditions which provide highly accurate layer composition, degree of dryness and layer thickness, all of which are extremely important to the successful preparation of electrodes as described herein. Once prepared by coating, which will usually take place in a planar or substantially planar configuration, if the electrode has been prepared on pliant support, it may be configured into almost any useful geometry by cutting, bending, etc. which will permit contact of the ion-selective membrane with a test solution. As described below, a preferred technique for using the electrode is in a substantially planar configuration by the application of a drop (less than about 50 $\mu$l) of test solution to the ion-selective membrane. A particularly useful mount for making measurements in this configuration is described in U.S. Pat. No. 4,053,381 entitled "Device for Determining Ionic Activity of Components of Liquid Drops."

Other additives such as dyes, plasticizers, etc., which may be desired for one reason or another may also be incorporated into the layer, so long as they do not interfere with the functions of the layer or components of the electrode.

Since the hydrophobic membrane layers described below are generally coated directly over the hydrophilic reference electrode, it is not entirely unexpected that, with certain embodiments of the electrodes described herein, adhesion problems between these two layers sometimes occur. In such instances, it may be useful to incorporate thin adhesion-improving or subbing layers between the reference electrode and the hydrophobic membrane. Care must, of course, be exercised to insure that such layer(s) do not interfere with the conductive contact between the membrane and the internal reference electrode and that no materials are introduced which might interfere with the reproducible potential established by the reference.

It is important that the electrolyte layer be dried prior to application of the overlying ion-selective membrane if the electrode is to be dry operative. If the hydrophobic ion-selective membrane is applied over the reference electrode while it is still wet or fully hydrated as suggested in the prior art then upon storage of the electrode at ambient conditions the water present in the reference electrode will migrate out of the electrode. Since the electrolyte layer is hydrophilic, i.e., water swellable, upon evaporation therefrom, the electrolyte layer apparently contracts while the overcoated hydrophobic membrane does not undergo any substantial contraction. Thus, the possibility exists for the occurrence of gaps or voids (i.e., reticulation) between the reference electrode and the hydrophobic membrane which will at least partially remove them from electrolytic contact until such time as the hydrophilic electrolyte solution is rehydrated and once again swells to a point where contact between the internal reference electrode and the membrane is reestablished. This phenomenon may lead to the requirement in the Genshaw et al patent that the membrane be coated over the electrolyte layer while the latter was still hydrated and which manifested itself in the Genshaw et al publication as a blistering or splitting of the membrane when the hydrophobic membrane was applied over a "dry" hydrophilic reference electrode and subsequently hydrated for use.

Electrodes using redox reference elements are prepared using techniques similar to those described above for the metal-insoluble metal-salt reference electrodes. Thus, the inert conductive layer, which may be a metal wire or foil or, alternatively, a dispersion of a particulate conductor such as carbon, is coated with a solution or dispersion of the redox species-containing layer, this latter layer dried and an ion selective membrane applied thereto as described above. Alternatively, the inert conductor and the redox species may both be incorporated into a matrix or binder composition and a single layer coated to provide the desired reference element. Of course, individual layers may be laminated in conducting contact to provide a similarly useful structure.

USE:

The ion selectivity of membrane electrodes can be observed by measuring the steady-state difference in electrical potential between solution 1 and solution 2 (both usually aqueous) in the cell arrangement schematically represented by the following:
Reference electrode 1/solution 1//membrane// solution 2/reference electrode 2

The calculations required to determine the ionic activity of solution 2 (generally the solution of unknown concentration) are derived from the well-known Nernst equation and are discussed in detail in a paper entitled "Cation Selectivity of Liquid Membrane, Electrodes Based upon New Organic Ligands" of Simon and Morf reported in the Pungor-edited reference cited above.

The electrode described herein incorporates within its structure substantially all of the components needed for making a potentiometric determination with the exception of a second reference electrode, the potential-indicating device and associated wiring so that in use the user merely needs to provide for contacting the sample with the ion-selective membrane, preferably by application of a small quantity of the sample to be analyzed (on the order of $<50$ $\mu l$) thereto and connection of appropriate lead wires. Automated dispensers for applying controlled amounts of sample to the electrode at the appropriate location are known and any such dispenser, or for that matter careful manual dispensing, may be used to contact the sample with the electrode. Specifically, dispensers of the type disclosed in U.S. Pat. No. 3,572,400 to Casner et al issued Mar. 23, 1971, may be adapted for applying small quantities (i.e., drops) to the surface of the electrode of the present invention. Other suitable dispensers are described in copending U.S. Patent Application Ser. No. 545,670 of R. Columbus filed on Jan. 30, 1975, and entitled METERING APPARATUS. Alternatively, when wires, cylinders, rods, etc., i.e., structures comprising other than planar surfaces which can be spotted, are used for the electrode, the electrode may actually be immersed in or contacted with the surface of the solution under analysis.

Second reference electrodes such as saturated calomel electrodes for use in combination with the integral electrodes of the present invention are also well known. In addition to such electrodes, reference elements of the type described herein as the internal references may also be used as the second or external reference electrode.

Similarly, potentiometers capable of reading the potentials generated in the ion-selective electrodes of the present invention are well known and, when properly connected as described hereinafter, can be used to give a sensory indication of the potential from which the ionic activity in the unknown solution may be calculated.

By incorporating computing capability into the potentiometric device it is, of course, possible to obtain direct readings of specific ionic concentrations in solution as a function of ionic activity.

As referred to numerous times herein, it is in their use that the electrodes of the present invention demonstrate their highly unexpected properties. Thus, while many prior art electrodes require preconditioning, wet storage or an equilibration period prior to use, the electrodes of the present invention, apparently because of their dried internal reference electrodes and the predetermined uniform thickness of their ion-selective membrane can be used without any need for conventional preconditioning, wet storage or equilibration protocols.

Figure 3:
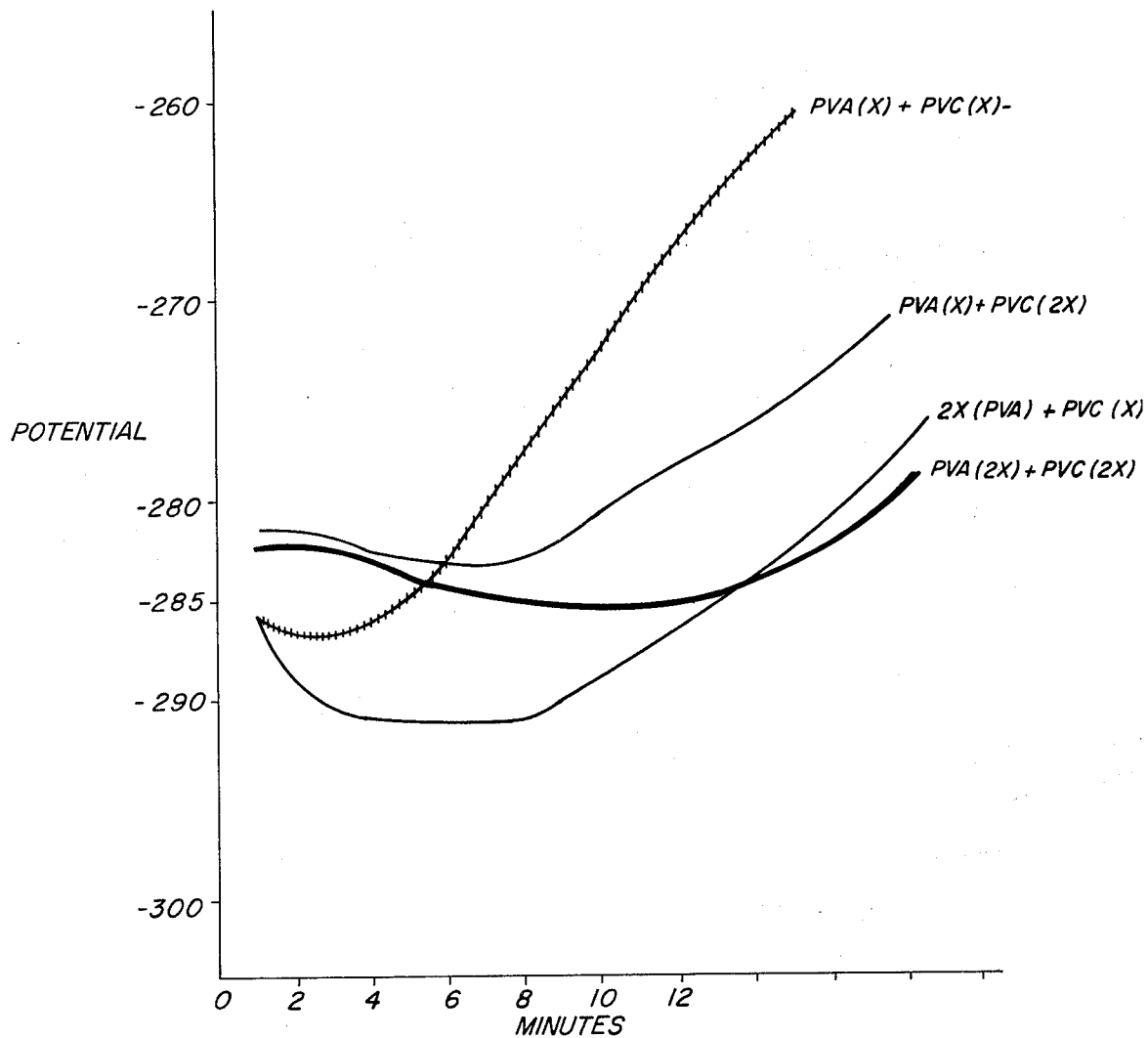
FIG. 3 shows typical traces of potential vs. time obtained using the ion-selective electrodes of the present invention as described in Example 47.

It has now been discovered that, when electrodes of the type described herein are stored under ambient conditions of the type normally encountered in a laboratory environment (most generally at or below RH about 65%) and subsequently spotted or otherwise contacted with samples of an aqueous ion-containing liquid as described above, under reproducible, known conditions, reproducible traces of the potential exhibited by these electrodes will define traces of potential vs. time as shown in FIG. 3. The phenomenon which is represented by this curve shape is "drift" which is defined hereinafter.

The shape of the curve produced by any specific electrode is determined by its composition and configuration. As described above, it is theorized that drift, particularly in electrodes as described herein, is related primarily to the thickness and composition of the ion-selective membrane which regulates the rate of water permeation of the electrode and the thickness and composition of the electrolyte layer which poises the potential of the internal reference electrode. Thus, the composition and configuration (e.g., physical dimensions such as thickness of the electrode) play a very significant role in the trace defined by any specific electrode or set of electrodes. Specific results attained by varying such thicknesses are shown in Example 47. It should, therefore, be apparent that if precise measurements are to be achieved using a series of disposable, single-use electrodes, it is important that the thickness and composition of the ion-selective membrane be carefully controlled and maintained at some predetermined uniform thickness from electrode to electrode and within regions of a single electrode intended for contact with the test sample. A lack of such controlled thickness uniformity will manifest itself as random or erratic drift which cannot be calibrated as described herein. Such drift will render it difficult, if not impossible, to calibrate a series of electrodes because variations in membrane thickness from electrode to electrode result in calibration curves having different shapes which cannot be related to ion activity or concentration in any meaningful fashion.

A study of FIG. 3 indicates that, after some appropriate interval, generally about 10 minutes, in electrode configurations of the type described herein, the potentials exhibited by the various electrodes begin to stabilize (i.e. the potential becomes nearly constant) thus indicating the attainment of the initial stages of steady state within the electrode. It is in the extremes of this stabilized portion of the potentiometric curve after wet storage or preconditioning that measurements of potential were made with the electrodes of the prior art and from which ion concentrations were calculated using the Nernst equation. We have discovered that using the electrodes of the present invention after storage at ambient conditions, the drift can actually be calibrated and that, using "calibrated drift," ionic concentration is reproducibly and accurately determinable almost immediately after contact of the surface of the electrode with the aqueous test solution. Such results are achieved without according the electrode any specialized storage treatment prior to use except to insure freedom from contamination as would be done for conventional laboratory glassware and equipment.

The depth and width of the trough will vary somewhat depending upon the ambient condition of use (primarily the relative humidity) and the thickness of the various layers (principally the hydrophobic membrane); however, these variations are easily compensated for by using either a differential measurement which compares the ion concentration of the unknown sample with that of a similar sample of known ion concentration (i.e., a calibrator or standard) simultaneously applied to an identical electrode, or by initially deriving calibration curves for the electrode for given sets of ambient conditions and subsequently relating the conditions of individual measurements to such calibration curves.

As will be described in the examples below, when electrodes prepared as described in U.S. Pat. No. 3,856,649 were stored "dry," i.e., at relative humidity below about 65%, and used as just described, a somewhat similar drift was observed; however, in these cases the drift was random and erratic, varied substantially from electrode to electrode and generally provided "uncalibratable" results, due most probably to the nonuniform thickness of the layers of such electrodes and the need for the reference electrode to be hydrated or equilibrated before true and uniform contact between the internal reference electrode and the hydrophobic membrane occurred.

Quite clearly, it is difficult to manufacture an electrode having layers of predetermined uniform thickness using a dipping technique, although such an electrode could conceivably be prepared using coating solutions of highly controlled viscosity and rotating the dipped work piece in a fashion which inhibits formation of a bulbous structure of non-uniform thickness. In view of the difficulties in use of such techniques, applicants prefer to prepare their electrodes in a planar format which not only simplifies manufacturing techniques but allows use by simply depositing a very small quantity (i.e., micro amounts on the order of less than about 50 $\mu$l) onto the planar electrode and measuring therefrom.

The following examples will serve to better demonstrate the successful practice of the present invention.

EXAMPLE 1

Ag/AgX Electrode

A sample of vacuum-deposited metallic silver on polyethylene terephthalate support ($\sim$10 mg Ag/dm$^2$) was prepared. A portion of this sample was treated for 5 minutes in the following solution:

| | |
|---|---|
| glacial acetic acid | 0.45 ml |
| sodium hydroxide | 0.20 g |
| potassium ferricyanide | 0.80 g |
| potassium bromide | 2.50 g |
| distilled water to 1 liter | |

The sample was then washed for 5 minutes in running distilled water.

Visual inspection revealed that partial conversion to silver bromide had occurred, leaving a contiguous layer of metallic silver adjacent the support. A narrow strip along one edge was dipped briefly in a thiosulfate bath to uncover the silver layer for purposes of making electrical contact.

Measurements of the electrochemical response were performed by applying small samples of aqueous solutions varying in Br$^-$ activity to the silver bromide layer. A linear response, with approximately theoretical slope (Nernst equation), was observed.

EXAMPLE 2

A Ag/AgX half-cell was prepared as described in Example 1 except that the conversion conditions were 30 seconds in a solution containing 8.45 g/l of potassium chlorochromate.

Measurements of electrochemical response were performed and showed linear potential response with varying Cl$^-$ and Ag$^+$ activity.

EXAMPLE 3

Laminated Ion-Selective Electrode

A silver-silver chloride film on polyethylene terephthalate was prepared as described in Example 2, 7.6 g/m$^2$ total silver with 15% conversion to AgCl (1.16 g/m$^2$) and then coated with a 5% polyvinyl alcohol (PVA)-0.2 M KCl solution (1.5 g KCl, 5.0 g PVA/m$^2$). After the PVA layer was dried by heating to 130° F. for 10 minutes, a precast ion-selective membrane comprising 0.50 g/m$^2$ of valinomycin (VAL), 40.4 g/m$^2$ of polyvinyl chloride (PVC) and 100.2 g/m$^2$ of bromophenyl phenyl ether (BPPE) as carrier solvent was manually laminated on top of the film coating.

The resulting ion-sensitive electrode, represented as Ag/AgCl/PVA-KCl/ion-selective membrane was tested by:
(1) connecting the silver-silver chloride film to the high-impedance input of a volt meter; and
(2) suspending a drop (25–50 μl) of the KCl solution to be measured from the tip of a saturated NaNO$_3$ salt bridge which was connected to an external reference electrode (Hg/Hg$_2$CL$_2$) which was in turn connected to the reference input of the volt meter, and contacting the drop to the surface of the electrode. The complete potentiometric cell is represented by: Hg/HgCl$_2$/KCl (X M) test/ion-selective membrane, PVA-KCl/AgCl/Ag.

A linear semilogarithmic response to potassium ion was observed with a slope of 57 mv/decade over the range pk+ 1 to 4.

EXAMPLE 4

Coated Ion-Selective Electrode

An electrode was prepared as in Example 3 except that the ion-selective membrane comprising 0.58 g/m$^2$ VAL, 22.9 g/m$^2$ polyvinyl chloride and 111.2 g/m$^2$ BPPE was coated directly onto the KCl-PVA layer rather than being laminated as in Example 3.

This integral electrode was tested as in Example 3 and exhibited a linear semilogarithmic potassium ion response having a slope of 55 mv/decade.

EXAMPLE 5

Reference Electrolyte Composition Variations

A series of electrodes were prepared utilizing a variety of surfactants and water-soluble polymers as binders for KCl in the reference electrolyte solution. The polymers included polyvinyl alcohol (PVA), deionized gelatin and polyacrylamide (PAM) (see Table 1). Unless otherwise noted, all electrodes contained 1.5 g/m$^2$ KCl. These electrodes were then laminated with a precast ion-selective membrane of the composition described in Example 3. The resulting electrodes were then evaluated as described in Example 3, with the results shown in Table 1 below.

Table 1

| | Internal Reference Element Binder Variations | | | |
|---|---|---|---|---|
| Test # | Binder | Spreading Agent g/m$^2$ | Response mv/decade | Range |
| 1 | PVA | — | 56 | $10^{-4} \to 10^{-1}$M K+ |
| 2 | PVA | — | 55 | $10^{-4} \to 10^{-1}$M K+ |
| 3 | PVA | 3.0 10G* | 53 | $10^{-4} \to 10^{-1}$M K+ |
| 4 | PVA | 4.6 Saponin | 57 | $10^{-4} \to 10^{-1}$M K+ |
| 5 | gelatin | .02 PEG** | 51 | $10^{-4} \to 10^{-1}$M K+ |

Table 1-continued

| | Internal Reference Element Binder Variations | | | |
|---|---|---|---|---|
| Test # | Binder | Spreading Agent g/m$^2$ | Response mv/decade | Range |
| 6 | PAM | .02 PEG** | 53 | $10^{-4} \to 10^{-1}$M K+ |

*Surfactant 10G is a nonyl phenyl polyglycidol commercially available from Olin-Mathieson, N.Y.
**Polyethylene Glycol The data of Table 1 demonstrate that the electrodes prepared as described give a linear potassium ion response with a slope between 51 and 57 mv/decade.

EXAMPLES 6–16

Ion-Selective Membrane Composition

A number of electrodes, both laminated and coated, were prepared to examine the effect of variations in the composition of the ion-selective membrane on the response of the electrode.

The elements were evaluated as described in Example 3 with the results shown in Table 2 below.

Table 2

| VALINOMYCIN - PVC - BPPE Variations | | | | |
|---|---|---|---|---|
| Fixed Components of Coated Electrodes | | | | |
| 7.6 g/m$^2$ Total Ag-1.16 g/m$^2$ AgCl, 5.0 g/m$^2$ PVA, 0.82 g/m$^2$ KCl | | | | |
| | g/m$^2$ | | Response | |
| VAL | PVC | BPPE | mv/decade | Range |
| 6 0.1 | 5 | 5 | none | — |
| 7 0.1 | 5 | 10 | none | — |
| 8 0.1 | 10 | 10 | poor | — |
| 9 0.5 | 10 | 20 | poor | |
| 10 0.5 | 15 | 40 | 57 | $10^{-4}$–$10^{-1}$M K+ |
| Fixed Components of Laminated Electrodes | | | | |
| 7.6 g/m$^2$ Total Ag-1.16 g/m$^2$ AgCl, 5.0 g/m$^2$ PVA, 1.49 g/m$^2$ KCl | | | | |
| 11 0.5 | 10 | 10 | none | — |
| 12 0.5 | 10 | 20 | 48 | $10^{-4} \to 10^{-1}$M K+ |
| 13 0.5 | 10 | 40 | 57 | $10^{-3} \to 10^{-1}$M K+ |
| 14 0.5 | 10 | 25 | 51 | $10^{-4} \to 10^{-1}$M K+ |
| 15 0.2 | 40 | 80 | 45 | $10^{-4} \to 10^{-1}$M K+ |
| 16 0.1 | 40 | 80 | nonlinear | |

The data in Table 2 illustrate the following effects as a function of variations of VAL, BPPE and PVC in the electrode format:
A. Less than 0.2 g/m$^2$ of valinomycin in the membrane results in either marginal or no potassium ion response.
B. BPPE/PVC ratios of less than 1:1 give dry unresponsive membranes. In general, carrier-solvent-to-polymer ratios of between 1:1 to 5:2 provide useful membrane layers.

EXAMPLES 17–23

Ion-Selective Membrane Composition

A number of electrodes, both laminated and coated, were prepared to demonstrate the utility of other polymers in the ion-selective membrane layer of the electrode. Polymers which were tested include Butvar B76 (a polyvinyl butyral available from Monsanto Chemical Co.), Estane 5107F1 (an aromatic polyurethane available from B. F. Goodrich), VYNS (a PVC/PVA$_c$*-90/10 copolymer available from Union Carbide) and Silastic ® 731RTV (a silicone rubber from Dow Corning, Midland, Michigan). After preparation, the electrodes were evaluated as described in Example 3, with the results shown in Table 3 below.

*PVA$_c$=polyvinyl acetate

Table 3

Polymer Variations
Fixed Components 7.6 g/m² Total Ag, 1.16 g/m² AgCl, 5.0 g/m² PVA, 1.5 g/m² KCl

| Test # | VAL | Polymer | g/m² BPPE | mv/dec Response | Range |
|---|---|---|---|---|---|
| 17 | 0.5 | 10 PVC | 25 | 51 | $10^{-4} \rightarrow 10^{-1}$ M K$^+$ |
| 18 Lamimated | 0.5 | 10 VYNS | 25 | 42 | $10^{-4} \rightarrow 10^{-1}$ M K$^+$ |
| 20 | 0.5 | 40 Estane | 80 | 58 | $10^{-4} \rightarrow 10^{-1}$ M K$^+$ |
| 21 | 0.5 | 40 (1:1, Estane 5107F1 PVC) | 80 | 58 | $10^{-4} \rightarrow 10^{-1}$ M K$^+$ |
| 22 Coated or Laminated | 0.5 | 40 PVC | 100 | 55 | $10^{-4} \rightarrow 10^{-1}$ M K$^+$ |
| 23 | 3.1 | 116 RTV Silastic ® | 100 | 56 | $10^{-4} \rightarrow 10^{-1}$ M K$^+$ |

The data of Table 3 illustrate that all of the polymers tested are useful in the present electrode configuration.

EXAMPLES 24–38

Ion-Selective Membrane Composition
(Carrier-Solvents)

A series of electrode were prepared to compare bromophenyl phenyl ether (BPPE) with other possible carrier solvents for the membrane layer. The other solvents which were tested include the following: 3-methoxyphenyl phenyl ether (3 MPPE), 4-methoxyphenyl phenyl ether (4MPPE), dimethylphthalate (DMP), dibutylphthalate (DBP), dioctylphenylphosphonate (DOPP) and bis(2-ethylhexyl)phthalate (BEHP) and dibutyl sebacate (DBS).

The integral electrodes were evaluated in the manner described in Example 3 with the results shown in Table 4 below.

Table 4

Carrier-Solvent Variations

| Test # | VAL | PVC | g/m² Solvent | mv/dec Response | Range |
|---|---|---|---|---|---|

Laminated Electrodes
7.6 g/m² Total Ag, 1.16 g/m² AgCl, 5.0 g/m² PVA, 1.5 g/m² KCl

| | | | | | |
|---|---|---|---|---|---|
| 24 | 0.5 | 40 | 60 4MPPE | 55 | $10^{-4} \rightarrow 10^{-1}$ M K$^+$ |
| 25 | 0.5 | 40 | 70 4MPPE | 50 | $10^{-4} \rightarrow 10^{-1}$ M K$^+$ |
| 26 | 0.5 | 40 | 80 4MPPE | 56 | $10^{-4} \rightarrow 10^{-1}$ M K$^+$ |
| 27 | 0.5 | 40 | 90 4MPPE | 52 | $10^{-4} \rightarrow 10^{-1}$ M K$^+$ |
| 28 | 0.5 | 40 | 80 3MPPE | 52 | $10^{-4} \rightarrow 10^{-1}$ M K$^+$ |
| 29 | 0.5 | 40 | 100 BPPE | 55 | $10^{-4} \rightarrow 10^{-1}$ M K$^+$ |

Laminated Electrodes
3.4 g/m² Total Ag, 0.76 g/m² AgCl, 5.0 g/m² PVA, 1.5 g/m² KCl

| | | | | | |
|---|---|---|---|---|---|
| 30 | 0.5 | 40 | 100 DMP | 33 | $10^{-4} \rightarrow 10^{-1}$ M K$^+$ |
| 31 | 0.5 | 40 | 100 DBP | 49 | $10^{-4} \rightarrow 10^{-1}$ M K$^+$ |
| 33 | 0.5 | 40 | 100 BPPE | 55 | $10^{-4} \rightarrow 10^{-1}$ M K$^+$ |

Coated Electrodes
7.6 g/m² Total Ag, 1.16 g/m² AgCl, 5.0 g/m² PVA, 1.5 g/m² KCl

| | | | | | |
|---|---|---|---|---|---|
| 34 | 0.5 | 10 | 25 BPPE | 51 | $10^{-4} \rightarrow 10^{-1}$ M K$^+$ |
| 35 | 0.5 | 10 | 25 MPPE | 50 | $10^{-4} \rightarrow 10^{-1}$ M K$^+$ |
| 36 | 0.5 | 10 | 25 MPPE | 55 | $10^{-4} \rightarrow 10^{-1}$ M K$^+$ |

Coated Electrodes
6.6 g/m² Total Ag - 0.44 g/m² AgCl, 4.84 g/m² PVA, 1.45 g/m² KCl, 0.1 g/m² Triton X-100 (octylphenoxy polyethoxy ethanol, commercially available from Rohm and Haas Co.)

| | | | | | |
|---|---|---|---|---|---|
| 37 | 0.5 | 10 | 25 DBS | 52 | $10^{-4} \rightarrow 10^{-1}$ M K$^+$ |
| 38 | 0.5 | 10 | 25 BEHP | 57 | $10^{-4} \rightarrow 10^{-1}$ M K$^+$ |

The data in Table 4 illustrate that the use of the phenyl ethers, phthalates and the sebacate as carrier-solvents results in electrodes which give good potassium ion response.

EXAMPLE 39

Electrodes were prepared and evaluated as described in Example 3 using various combinations of ion carrier and coating solvents in the membrane layer. The results are shown in Table 5.

BEHP = Bis ethylhexyl phthalate
THF = tetrahydrofuran
MEK = methyl ethyl ketone
DDP = didodecyl phthalate The composition of the membranes were as follows:
0.48 g/m² valinomycin
9.76 g/m² polyvinylchloride
15.00 g/m² carrier-solvent

Table 5

| Carrier Solvent | Coating Solvent | Slope (Range of Multiple Measurements) |
|---|---|---|
| BEHP | THF | 51.9–59.3 |
| BEHP | MEK | 56.3–58.9 |
| DDP | THF | 56.2–59.3 |
| DDP | MEK | 53.5–58.6 |

EXAMPLE 40

Electrode Sensitivity

A coated electrode was prepared as described in Example 3 and tested for selectivity as described below.

COMPOSITION 6.9 g/m² Total Ag
1.4 g/m² AgCl
1.5 g/m² KCl
5.0 g/m² PVA
9.68 g/m² PVC
24.2 g/m² DDP
0.48 g/m² VAL

EVALUATION

The normal level for potassium ion in blood serum is about 4 meq/liter while that for sodium is 30 to 40 times higher. it is important, therefore, that sodium ion not interfere with the potassium ion measurement to any substantial degree. To examine the extent to which sodium ion interferes with the potassium ion response, the selectivity coefficient $K_{K^+/Na^+}$, defined by the equation:

$$E = E° + 2.303 \frac{RT}{F} \log [(a_{K^+} + (K_{K^+/Na^+})a_{Na^+})]$$

was determined for the above-described coating. Measurements on this coating, using the constant interferent method gave a value of $1 \times 10^{-3}$ in 0.15 M NaCl. In a solution containing 5 mM K⁺ and 150 mM Na⁺, the sodium response exhibited by this coating represents about a 3% interference. Thus, small variations in Na⁺ over the clinical range, i.e., 0.12 M to 0.16 M Na⁺ result in less than 1% variation in the interference.

EXAMPLE 41

A redox reference electrode having a double-layer structure was prepared by coating poly(ethylene terephthalate) film support with a conductive layer coprising deionized gelatin (9.7 g/m²), particulate carbon (15.5 g/m²) and Triton X-100 (a polyethoxy ethanol commercially available from Rohm & Haas Co.) (0.28 g/m²) and a redox layer comprising deionized gelatin (4.85 g/m²) as a binder, potassium ferricyanide (5.4 meq/m²), and potassium ferrocyanide (5.4 meq/m²). The resulting reference electrode was manually laminated to a precast ion-selective membrane comprising valinomycin (VAL) (0.49 g/m²), bis(2-ethylhexyl)phthalate (BEHP) (14.5 g/m²) and polyvinyl chloride (PVC) (9.2 g/m²).

The resulting composite ion-selective electrode was tested in the following cell:

| 0.15M NaCl CE | 50λ drop of 0.15 M NaCl containing 10⁻¹ to 10⁻⁴ KCl | ion-selective electrode |

Table 6

| Potassium Ion Response Fe(II)/Fe(III) Internal Reference | |
|---|---|
| KCl M | 2 Min. (mv) |
| $10^{-4}$ | −59.0 |
| $10^{-3}$ | −3.7 |
| $10^{-2}$ | +54.4 |

Table 6-continued

| Potassium Ion Response Fe(II)/Fe(III) Internal Reference | |
|---|---|
| KCl M | 2 Min. (mv) |
| $10^{-1}$ | +108.2 |

The emf at 2 minutes shows a linear semilogarithmic dependence on potassium ion concentration with a slope of 57 mv/decade. The potential drifts with time after spotting the element with 50 μl of test solution. The magnitude of the reproducible drift is about 0.1 mv/minute between 2 and 10 minutes.

EXAMPLE 42

Ion-Selective Electrode Utilizing Single-Layer Fe(II)/Fe(III) Reference Electrode A reference electrode having a single-layer structure was prepared by coating polyethylene terephthalate film support with a layer comprising deionized gelatin as binder (4.3 g/m²), particulate carbon (6.9 g/m²), octylphenoxy polyethoxy ethanol (0.12 g/m²), potassium ferricyanide (7.5 meq/m²) and potassium ferrocyanide (7.5 meq/m²). The resulting reference electrode was then manually laminated to a precast ion-selective membrane comprising valinomycin (0.49 g/m²), BEHP (14.5 g/m²) and PVC (9.2 g/m²).

The resulting integral electrode was evaluated in the manner described in Example 40 with the following results:

Table 7

| Potassium Ion Response of Integral Electrode Having "Single-Layer" Fe(II)/Fe(III) | |
|---|---|
| KCl M | 2 Min. (mv) |
| $10^{-4}$ | −64.0 |
| $10^{-3}$ | −5.8 |
| $10^{-2}$ | +49.6 |
| $10^{-1}$ | +102.4 |

The emf at 2 minutes shows a linear semilogarithmic dependence on potassium ion concentration with a slope of 55 mv/decade. The potential of this "single-layer" format drifts at a rate of about 1.0 mv/minute between 2 and 10 minutes.

EXAMPLE 43

Electrode Utilizing Double Layer Co(II)/Co(III) Reference Electrode

A reference electrode having a double-layer structure was prepared by coating polyethylene terephthalate film support with a conductive layer comprising deionized gelatin as binder (9.8 g/m²), particulate carbon (15.6 g/m²), saponin (0.2 g/m²) and bis(vinylsulfonylmethyl)ether (0.1 g/m²) followed by a redox layer comprising deionized gelatin (10.8 g/m²) octylphenoxy polyethoxy ethanol (0.22 g/m²), bis(vinylsulfonylmethyl)ether (0.22 g/m²), Co(terpyridyl)₂(BF₄)₂ (210 μmoles/m²). The resulting coating was then soaked for 30 minutes in 0.1 N KCl, dried in room air for 24 hours and then manually laminated to a precast ion-selective membrane comprising VAL (0.49 g/m²²), BEHP (14.5 g/m²) and PVC (9.2 g/m²).

The bathing step in the preparation procedure was included in this example as a method of absorbing potassium ion into the redox layer to poise the potential of the membrane. This step was not necessary in Examples 40 and 41 because the ferro/ferricyanide buffer was prepared with potassium salts.

The evaluation of the element was carried out as in Example 40 with the following results:

Table 8

Potassium Ion Response of Integral Electrode Having "Double-Layer" Co(II)/Co(II) Internal Reference

| KCL M | Cell Emf at 2 Min. (mv) |
|---|---|
| $10^{-4}$ | $-237.4$ |
| $10^{-3}$ | $-183.2$ |
| $10^{-2}$ | $-126.3$ |
| $10^{-1}$ | $-68.5$ |

The emf at 2 minutes shows a linear semilogarithmic dependence on potassium ion concentration with a slope of 57 mv/decade. The potential drifts at a rate of about 0.1 mv/minute over 3 to 10 minutes.

EXAMPLE 44

Electrodes were prepared as described in U.S. Pat. No. 3,856,649. During and after preparation, the electrodes were maintained at 100° F. and 66% RH. Evaluation of these electrodes immediately after preparation indicated response with little drift and linear slopes of about 60 mv/decade over the range of $10^{-4}$ to $10^{-1}$ M KCl. Storage of identical electrodes at ambient laboratory conditions of about 35–40% RH for 1 to 15 days with subsequent evaluation by dipping the electrodes into solutions of known KCl concentration and reading as described above in Example 3 resulted in erratic drifts of from 2–4 mv/min. The rate of drift slowed until after about 10–14 minutes the electrode demonstrated a relatively stable positive drift of about 1 mv/min. Subsequent uses of the same electrodes gave smaller drifts, indicating that in use the electrode, as expected, tends to equilibrate as the internal reference becomes hydrated and thus provides more accurate determinations with continued wetting.

EXAMPLE 45

Wire electrodes having a generally bulbous shape were prepared using the dipping techniques suggested by Genshaw et al except that the electrolyte layer was dried at 135° F. for a period of 10 minutes prior to application of the ion-selective membrane, to simulate the preparation of electrodes according to the present invention wherein the hydrophilic layer is dried prior to application of the ion-selective membrane, but without control of layer-thickness uniformity. Storage of these electrodes at ambient conditions (i.e., 35–40% RH), and subsequent use yielded curves which demonstrated large, random initial drifts of from 16 to 57 mv/(minute) for from 2 to 10 minutes. When allowed to soak in $10^{-1}$ M KCl, the blistering or bursting of the outer membrane as described in the Genshaw publication was observed only after nine days of soaking in such a solution. Before bursting, linear Nernstian responses over the range 1–10 mM K+ were observed after an initial soaking of several hours.

EXAMPLE 46

A wire electrode was prepared as described in Example 45 except that the ion-selective membrane layer was dried at 85° F. instead of 35° F. When used after storage at preselected ambient conditions of relative humidity below about 80% and without preconditiong these electrodes exhibited large random drift up to about 15 to 16 minutes when drift stabilized and linear Nernstian response was observed.

From the foregoing it should be apparent that electrodes prepared according to the techniques described in Genshaw et al exhibit linear Nernstian response when properly preconditioned to achieve a hydrated state; however, without such preconditioning their behavior is random and erratic and incapable of calibration under normal ambient conditions of use without some appropriate induction period.

As the foregoing Examples 44–46 show, electrodes prepared as described in the prior art which comprise an ion-selective membrane of varying thickness in regions thereof intended for contact with a sample for analysis demonstrate erratic drift which cannot be calibrated.

EXAMPLE 47

Coated electrodes were prepared as described in Example 4, but with the following compositions for the reference electrolyte layer and the ion-selective membrane:

| Reference Electrolyte Layer | PVA | 4.8 g/m² |
|---|---|---|
| | KCl | ~2.4 g g/m² |
| Ion-Selective Membrane | PVC | 9.7 g/m² |
| | DDP | 14.6 g/m² |
| | VALINOMYCIN | 0.5 g/m² |

FIG. 3 shows the shape of E vs. Time curves obtained by varying the thickness of the foregoing layers by doubling the laydown of the respective compositions. As is clear these curves have different shapes, however, each is calibratable and can provide precise and accurate indications of potential related to ion activity and concentration.

EXAMPLE 48

Coated electrodes were prepared as described in Example 4, but with the following compositions for the reference electrolyte layer and the ion-selective membrane:

| Reference Electrolyte Layer | | |
|---|---|---|
| Gelatin | 5 | g/m² |
| NaCl | 2.5 | g/m² |
| Surfactant | .09 | g/m² |
| Ion-Selective Membrane | | |
| PVC (1.8% carboxylated) | 10 | g/m² |
| Tris (2-ethylhexyl)phosphate | 12.5 | g/m² |
| Sodium Tetraphenyl Boron | .6 | g/m² |
| Surfactant | .06 | g/m² |

When drop size samples of aqueous sodium ion solutions were applied to this electrode a Nernstian slope of 57 mv/dec was observed.

EXAMPLE 49

Coated electrodes were prepared as described in Example 48, but with the following composition for the ion-selective membrane:

| Ion-Selective Membrane | | |
|---|---|---|
| PVC | 10 | g/m² |
| 4-octyltrifluoroacetophenone | 5 | g/m² |
| Didodecylphthalate | 10 | g/m² |

-continued

| | | |
|---|---|---|
| Trioctylpropylammonium Chloride | .5 | g/m$^2$ |

This electrode demonstrated a slope of 27 mv/dec when an aqueous sample containing $CO_3^=$ was applied to the ion-selective membrane.

EXAMPLE 50

Coated electrodes were prepared as described in Example 48, but with the following composition for the ion-selective membrane:

| | | |
|---|---|---|
| Ion-Selective Membrane | | |
| PVC | 10 | g/m$^2$ |
| Didodecyldimethylammonium Chloride | 15 | g/m$^2$ |
| Didodecylphthalate | .25 | g/m$^2$ |
| Trioctylpropylammonium Chloride | .25 | g/m$^2$ |

This electrode demonstrated a Nernstian slope of 58 mv/dec when contacted with aqueous solutions containing chloride ion.

EXAMPLE 51

Coated electrodes were prepared as described in Example 48, but with the following composition for the ion-selective membrane:

The ion-selective membrane layer contains:

| | | |
|---|---|---|
| PVC | 10 | g/m$^2$ |
| Ion Carrier | 1 | g/m$^2$ |
| TPPP | 15 | g/m$^2$ |
| DC-510 Surfactant | 0.06 g/m$^2$ | (a polysiloxane surfactant from Dow-Corning) |

Evaluation of these electrodes as described above produced the results shown in Table 9.

Table 9

| | Integral Electrodes | | |
|---|---|---|---|
| | Potentiometric Response | | |
| | Slope | Selectivity | |
| Ion-Carrier | mV/decade | K$_{Na+/K+}$ | Comments |
| Antamanide* | 46 | — | Very rapid drift |
| TMTNTF** | — | — | Very irreg. drift |
| EBGADBA*** | — | — | Wild drift |
| None | — | — | Wild drift |
| D12C4**** | 46 | 0.8 (high) | |
| Na+ Monensin | 49 | 1 (high) | |
| Methyl Monensin | 57 | 0.4 | Very flat drift |

*A cyclic dipeptide occurring in *Amanita phalloides*, a fungus.
**1,5,9,13-tetramethyl-1,5,9,13-tetranonyl tetrafuro-16-crown-4-ether.
***Ethylene-bis-(glycolic acid dibenzylamide).
****Dicyclohexyl-12-crown-4-ether.

Thus, in the integral coated format, methyl monensin also shows superior potentiometric response, a very good selectivity constant for sodium ions over potassium ions and a very desirable flat electrode drift over other known ion carriers including sodium monensin, as shown in Table II.

EXAMPLE 52

Laminated electrodes were produced as described in Example 3, but with the following composition for the ion-selective membrane:

| | |
|---|---|
| PVC | 40 g/m$^2$ |
| Ion Carrier | 1 g/m$^2$ |
| TPPP | 80 g/m$^2$ |

Evaluation of these electrodes according to the procedures described hereinabove produced the results shown in Table 10.

Table 10

| | Laminated Electrodes | |
|---|---|---|
| | Potentiometric Response | |
| | Slope | Selectivity |
| Ion Carrier | mV/decade | K$_{Na+/K+}$ |
| Monensin free acid | 52 | 1.0 (high) |
| Li+ Monensin | 45 | 4.0 (high) |
| K+ Monensin | 42 | 2.0 (high) |
| Methyl Monensin | 55 | 0.4 |

Thus, electrodes prepared by laminating various membranes over the reference element show that methyl monensin is superior to the ionic forms of monensin, i.e., the lithium or potassium salts or the free acid of monensin in both potentiometric response (slope) approaching the ideal of 59 mV/decade and the selectivity constant (desirably below 0.6 K$_{Na+/K+}$).

Although the multilayer electrode elements of the present invention have been described primarily in connection with the potentiometric quantitation of alkali metal and alkaline earth ions, the structures, compositions and techniques described herein are equally applicable to the assembly of electrodes for the analysis of other cations such as $NH_4^+$ and anions such as $SO_3^=$ principally by the selection of appropriate ion-specific carriers for the ion-selective membrane, and such electrodes are clearly within the contemplated scope of the instant invention.

Furthermore, it is within the scope of the instant application to incorporate protective overlayers for the electrode which may serve merely to protect the surface thereof, increase mechanical strength, or serve multiple additional purposes such as permitting selective permeability to a specific ion, or permeability only to a particular gaseous component of a solution under test, for example, oxygen or carbon dioxide.

It is also contemplated that electrodes of the type described herein would be useful in combination with overlayers containing enzymes which act upon a substrate specifically and selectively to release ions which can be quantified by the electrode.

Furthermore, although the internal reference electrodes of this invention have been described as and exemplified by metal/metal salt and redox couple electrodes, it will be apparent to the skilled artisan that metal/metal ion reference electrodes will be similarly useful and ion-selective electrodes incorporating such reference electrode are clearly within the contemplated scope of the appended claims.

While the invention has been described in detail with particular reference to preferred embodiments, thereof, it will be understood that variations and modifications can be effected within the spirit and scope of the invention.

We claim:

1. A dry-operative ion-selective electrode comprising:

(a) a dried internal reference electrode comprising the dried residue of a solution of a salt and a hydrophilic polymeric binder in a solvent for the polymer and the salt; and (b) in contact with said reference electrode a hydrophobic ion-selective membrane of predetermined uniform thickness in regions thereof intended for contact with a sample for analysis, said membrane comprising a hydrophobic binder having distributed therein an ion carrier dissolved in a carrier solvent.

2. The electrode of claim 1 further including a support, said reference electrode being disposed between said support and said membrane.

3. The electrode of claim 2 wherein said support comprises a polymeric material.

4. The electrode of claim 3 wherein said polymeric material is a cellulose acetate, poly(ethylene terephthalate), a polycarbonate or a polystyrene.

5. The electrode of claim 1 wherein said hydrophobic binder comprises a polymer selected from the group consisting of polyvinyl chloride, a polyurethane, carboxylated polyvinyl chloride, polymethine, a copolymer of poly(vinyl chloride) and poly(vinyl acetate), a silicone elastomer, a polycarbonate, a cellulose ester, a copolymer of polyvinyl chloride and polyvinylidene chloride, polyvinyl butyral, polyvinyl formal and polyvinyl alcohol.

6. The electrode of claim 1 wherein said ion carrier is selected from the group consisting of valinomycin, a cyclic polyether, tetraphenyl borate, a tetralactone, a macrolide acetone, a cyclic polypeptide, a quarternary ammonium salt, monensin, esters of monensin, A23187 and compounds of the formula

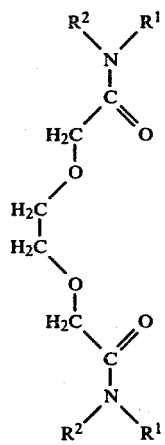

wherein:
I    $R^1$: —CH₃
     $R^2$: —(CH₂)n—COO—CH₂—CH₃
     wherein n = 1 or 10
II    $R^1$: —CH₃
     $R^2$: —(CH₂)₆—CH₃
III    $R^1 = R^2$: —CH₂—CH₂—CH₃
IV    $R^1$: —CH₂—CH₂—CH₃
     $R^2$: —CH₂—C—(CH₃)₃
V

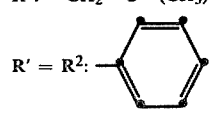

VI 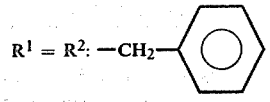

and
Compounds of the following structural formulas

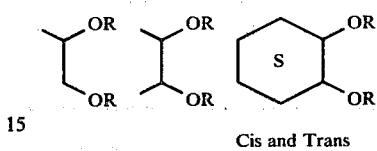

Cis and Trans

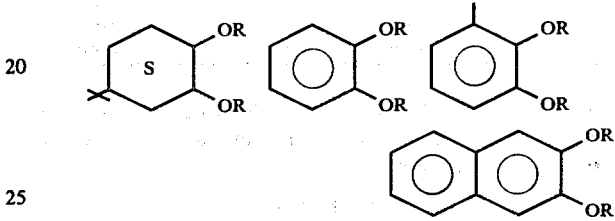

wherein:
(a) R=CH₂CON(CH₂CH₂CH₃)₂

$$R = CH_2CON-(CH_2)_{11}-CO_2CH_2CH_3 \atop {\phantom{R = }}\ \ \ CH_3 \qquad (b)$$

7. The electrode of claim 1 wherein said ion carrier solvent is selected from the group consisting of aromatic ethers, aliphatic ethers, phthalates, phosphates, phosphonates, adipates and sebacates.

8. The electrode of claim 1 wherein the weight ratio of said carrier solvent to said hydrophobic binder ranges from about 1:1 to about 5:2.

9. The electrode of claim 1 wherein the thickness of said membrane varies at most about 20% in regions intended for contact with a sample for analysis.

10. A dry-operative ion-selective electrode comprising:

(a) a dried internal reference electrode comprising a metal/metal salt reference electrode, said reference electrode comprising a conducting layer of a metal in contact with a layer of an insoluble salt of said metal, and a dried electrolyte layer comprising the dried residue of a water soluble salt having as an anion the anion of said metal salt layer and a hydrophilic polymeric binder in a solvent for the polymer and salt; and (b) in contact with the reference electrode a hydrophobic ion-selective membrane or predetermined uniform thickness in regions intended for contact with a sample for analysis said membrane comprising an ion carrier and a carrier solvent distributed in a binder.

11. The electrode of claim 10 wherein said hydrophilic binder comprises a member selected from the group consisting of polyvinyl alcohol, gelatin, agarose, polyacrylamide, polyvinyl pyrrolidone, polyhydroxyethyl methacrylate, poly(hydroxyethyl acrylate) and polyacrylic acid.

12. The electrode of claim 10 wherein said layer of insoluble salt comprises a halide salt of said metal.

13. The electrode of claim 10 further including a support which comprises an electrically insulating polymeric film, said conducting metal layer comprises silver, said layer of insoluble salt comprises a halide salt of silver, and said hydrophobic membrane comprises poly(vinyl chloride) and ion carrier selected from the group consisting of valinomycin and tetraphenyl boron and said carrier solvent is selected from the group consisting of cyclic ethers, sebacates, phthalates, adepates, phosphonates and phosphates.

14. A dry-operative ion-selective electrode comprising:
(a) a dried redox internal reference electrode comprising the dried residue of a redox couple, a hydrophilic binder and a solvent over an electrically conducting layer; and
(b) in contact with the reference electrode a hydrophobic, ion-selective membrane of predetermined uniform thickness in a region thereof intended for contact with a sample for analysis, said membrane comprising a hydrophobic binder having distributed therein an ion carrier and a carrier solvent.

15. The electrode of claim 14 wherein said conducting layer comprises a conductor selected from the group consisting of carbon, platinum, and nickel.

16. The electrode of claim 14 wherein said conductor is carbon.

17. The electrode of claim 14 wherein said conducting layer comprises a particulate conductor and a binder.

18. The electrode of claim 17 wherein said particulate conductor is particulate carbon.

19. The electrode of claim 14 wherein said hydrophilic polymer is selected from the group consisting of gelatin, polyvinyl alcohol, polyacrylic acid and poly(vinyl pyrrolidone).

20. The electrode of claim 14 wherein said redox couple comprises a material, a portion of which is in a first oxidation state and a portion of which is in a second oxidation state.

21. The electrode of claim 20 wherein the molar ratio of said portions is about 1.

22. The electrode of claim 21 wherein said redox couple comprises iron or cobalt complexes.

23. The electrode of claim 22 wherein said iron or cobalt complexes comprise, respectively, ferri/ferrocyanide ions and cobaltic/cobaltous terpyridyl ions.

24. The electrode of claim 14 wherein said hydrophobic binder comprises a polymer selected from the group consisting of polyvinyl chloride, polymethine, copolymers of poly(vinyl chloride) and poly(vinyl acetate), silicone elastomers, polycarbonates and cellulose esters.

25. The electrode of claim 14 wherein said ion carrier is selected from the group consisting of valinomycin, cyclid polyether, tetraphenyl borate, tetralactones, macrolide acetones, cyclic polypeptides, monensin, esters of monensin, A23187 and compounds of the formula

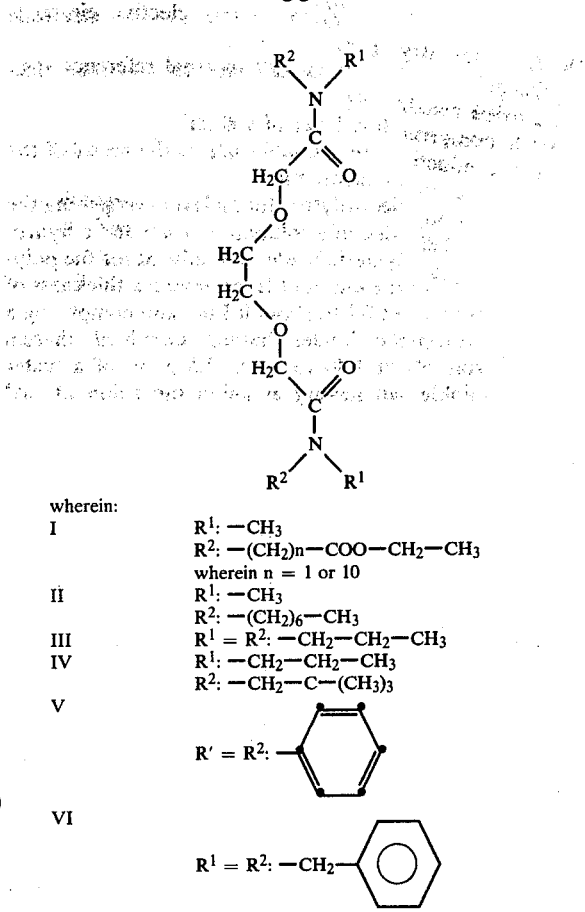

wherein:

I    $R^1$: —$CH_3$
    $R^2$: —$(CH_2)_n$—COO—$CH_2$—$CH_3$
    wherein n = 1 or 10

II    $R^1$: —$CH_3$
    $R^2$: —$(CH_2)_6$—$CH_3$

III    $R^1 = R^2$: —$CH_2$—$CH_2$—$CH_3$

IV    $R^1$: —$CH_2$—$CH_2$—$CH_3$
    $R^2$: —$CH_2$—C—$(CH_3)_3$

V    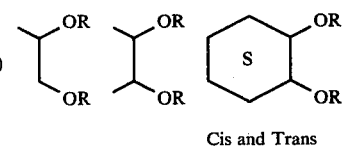

VI    $R^1 = R^2$: —$CH_2$—⟨phenyl⟩ and compounds of the following structural formulas

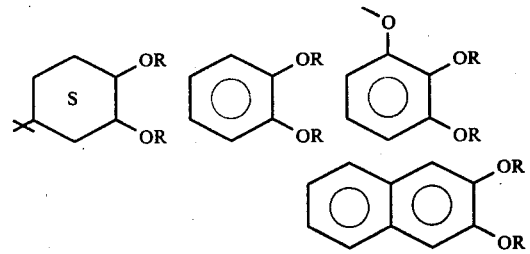

wherein:
(a) R=$CH_2CON(CH_2CH_2CH_3)_2$ (b) R = $CH_2CON$—$(CH_2)_{11}$—$CO_2CH_2CH_3$
            |
            $CH_3$ 26. The electrode of claim 14 wherein said ion carrier solvent is selected from the group consisting of aromatic and aliphatic ethers, phosphonates and phosphates, and mixtures thereof, phthalates and sebacates.

27. The electrode of claim 14 wherein the weight ratio of said carrier solvent to said binder ranges from about 1:1 to about 5:2.

28. A planar, dry-operative ion-selective electrode comprising:
(a) a dried metal/metal salt internal reference electrode comprising
  (1) a conducting layer of a metal,
  (2) a layer of an insoluble salt of the metal of the conducting layer, and
  (3) a dried electrolyte solution layer comprising the dried residue of a solution of a salt and a hydrophilic polymeric binder in a solvent for the polymer and the salt, said layer having a thickness of from about 0.1 to about 0.5 mil and comprising a hydrophilic binder having dissolved therein from about 1.40 to about 2.5 $g/m^2$ of a water soluble salt having as anion the anion of said metal salt layer, said conducting layer in contact with said layer of insoluble salt, and
(b) in contact with said electrolyte layer a hydrophobic ion-selective membrane having a predetermined uniform thickness of less than about 5 mil and comprising at least about 0.1 $g/m^2$ of an ion carrier dissolved in an ion carrier solvent dispersed in a binder the weight ratio of said carrier solvent to said binder ranging from about 1:1 to about 5:2.

29. The electrode of claim 28 wherein the thickness of said dry electrolyte layer is about 0.2 mil.

30. The electrode of claim 29 wherein said membrane comprises from about 0.3 to about 0.5 $g/m^2$ of said ion carrier and has a thickness of about 1 mil.